(12) United States Patent
Brookes

(10) Patent No.: US 7,179,589 B2
(45) Date of Patent: Feb. 20, 2007

(54) DETECTION OF NUCLEIC ACID POLYMORPHISM

(75) Inventor: Anthony J. Brookes, Uppsala (SE)

(73) Assignee: Dynametrix Ltd. (GB)

( * ) Notice: Subject to any disclaimer, the term of this patent is extended or adjusted under 35 U.S.C. 154(b) by 502 days.

(21) Appl. No.: 09/755,747

(22) Filed: Jan. 5, 2001

(65) Prior Publication Data

US 2001/0046670 A1    Nov. 29, 2001

Related U.S. Application Data

(63) Continuation-in-part of application No. PCT/GB99/03329, filed on Oct. 7, 1999.

(30) Foreign Application Priority Data

Oct. 8, 1998    (GB) ................................. 9821989.2

(51) Int. Cl.
*C12Q 1/68*    (2006.01)
(52) U.S. Cl. ........................................................ 435/6
(58) Field of Classification Search .................... 435/6, 435/91.1, 91.2; 536/23.1, 24.3, 24.31
See application file for complete search history.

(56) References Cited

U.S. PATENT DOCUMENTS

| | | | | |
|---|---|---|---|---|
| 4,824,776 | A * | 4/1989 | Heller ............................ | 435/6 |
| 5,789,167 | A * | 8/1998 | Konrad et al. .................. | 435/6 |
| 6,048,690 | A * | 4/2000 | Heller et al. .................... | 435/6 |
| 6,174,670 | B1 * | 1/2001 | Wittwer et al. ................. | 435/6 |
| 6,406,845 | B1 * | 6/2002 | Walt et al. ...................... | 435/6 |
| 2002/0109841 | A1 * | 8/2002 | Gould et al. | |

OTHER PUBLICATIONS

Ririe et al, "Product differentiation by analysis of DNA melting curves during the polymerase chain reaction" Anal. Biochem. (1997) 245:154-160.*

Drobyshev et al, "Sequence analysis by hybridization with oligonucleotide microchip: identification of b-thalassemia mutations" Gene (1997) 188:45-52.*

Spiess et al "Normalization of RNA hybridization signals by means of SYBR green II stained 28S or 18S ribosomal RNA and a phosphorimager".*

Stimpson et al, "Real-time detection of DNA hybridization and meltin on oligonucleotide arrays by using optical wave guides", Proc. Natl. Acad. Sci. (1995) 92:6379-6383.*

Jordan, Anal. Chem. (1997) 69:4939-4947.*

* cited by examiner

*Primary Examiner*—Jeffrey Fredman
(74) *Attorney, Agent, or Firm*—Joseph T. Leone, Esq.; DeWitt Ross & Stevens S.C

(57) ABSTRACT

This document describes a method of detecting DNA variation by monitoring the formation or dissociation of a complex consisting of: (a) a single strand of a DNA sequence containing the locus of a variation, (b) an oligonucleotide or DNA analogue probe specific for one allele of the variation and capable of hybridizing to the single strand (a) to form a duplex, a marker specific for the duplex structure of (a) plus (b) which forms a complex with the said duplex and reacts uniquely when interacting within the duplex, which comprises continually measuring an output signal indicative of interaction of the marker with duplex formed from the strand (a) and probe (b) and recording the conditions at which a change in reaction output signal occurs which is attributable to formation or dissociation of the complex and is thereby correlated with the strength with which the probe (b) has hybridized to the single strand (a). The method, termed Dynamic Allele Specific Hybridization (DASH), scores nucleotide differences in DNA sequences. Fluorescent markers are convenient as markers to underline variations in fluorescence resulting from denaturization or hybridization of the complex.

58 Claims, 13 Drawing Sheets

Figure 1.a.
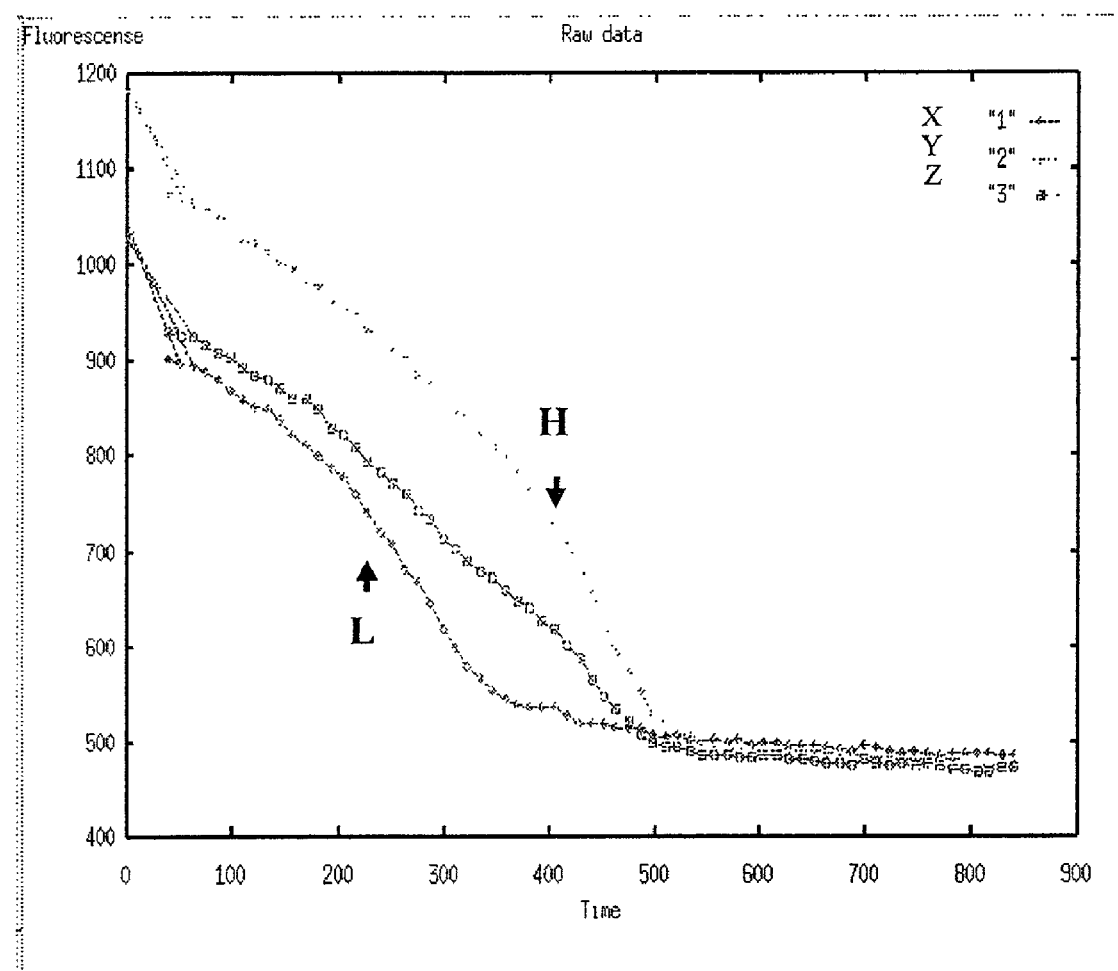

Figure 1.b.
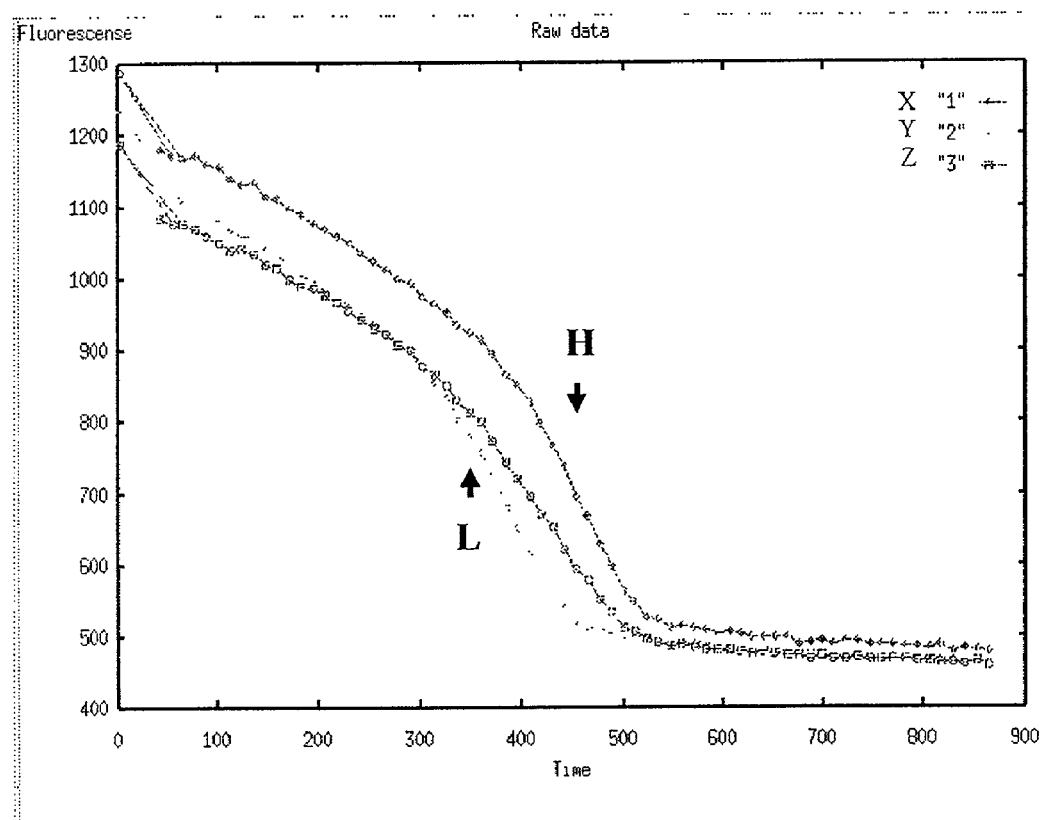

Figure 2.a.
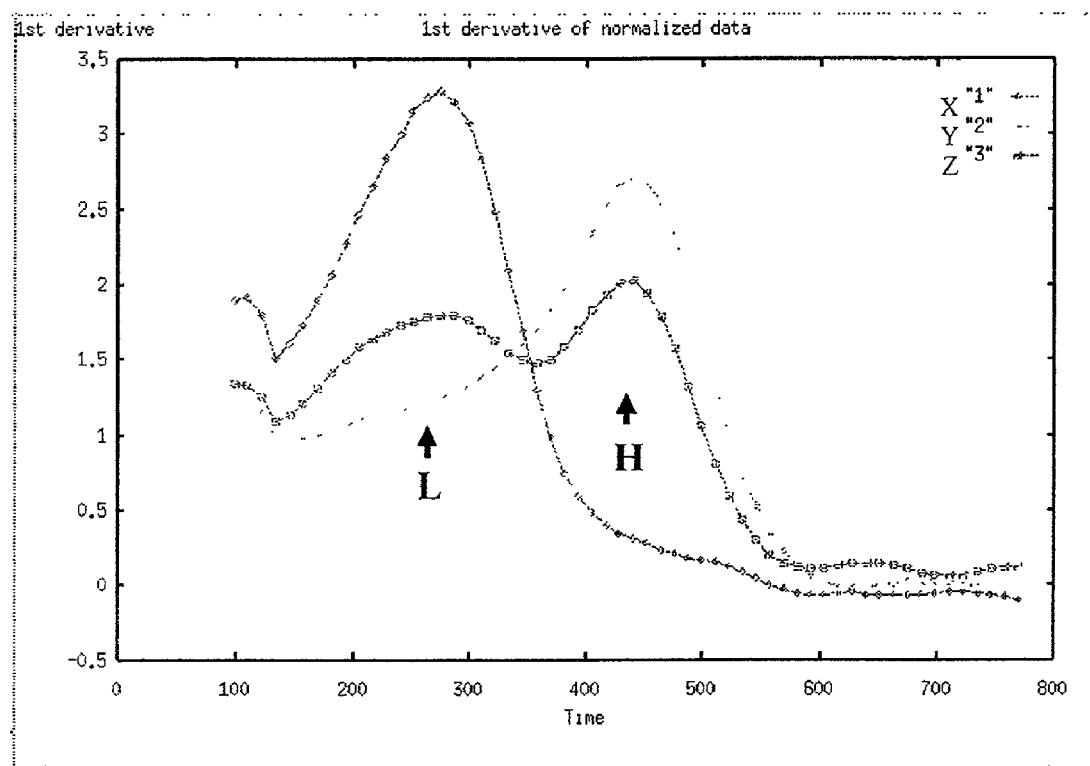

Figure 2.b.
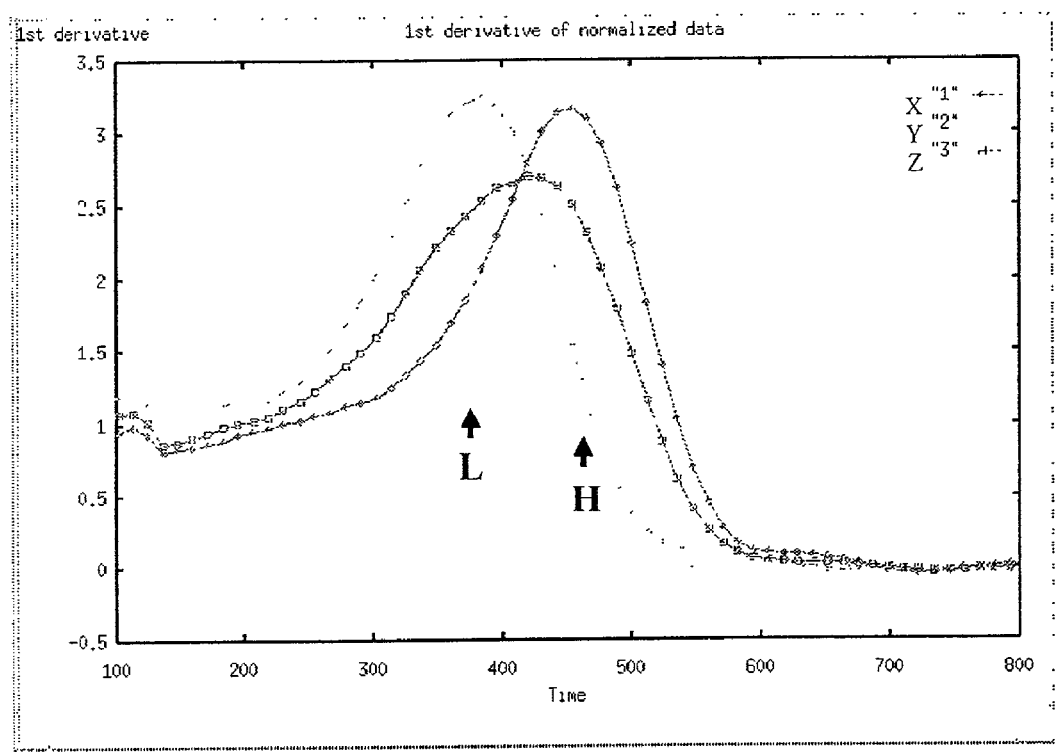

Figure 3.a.
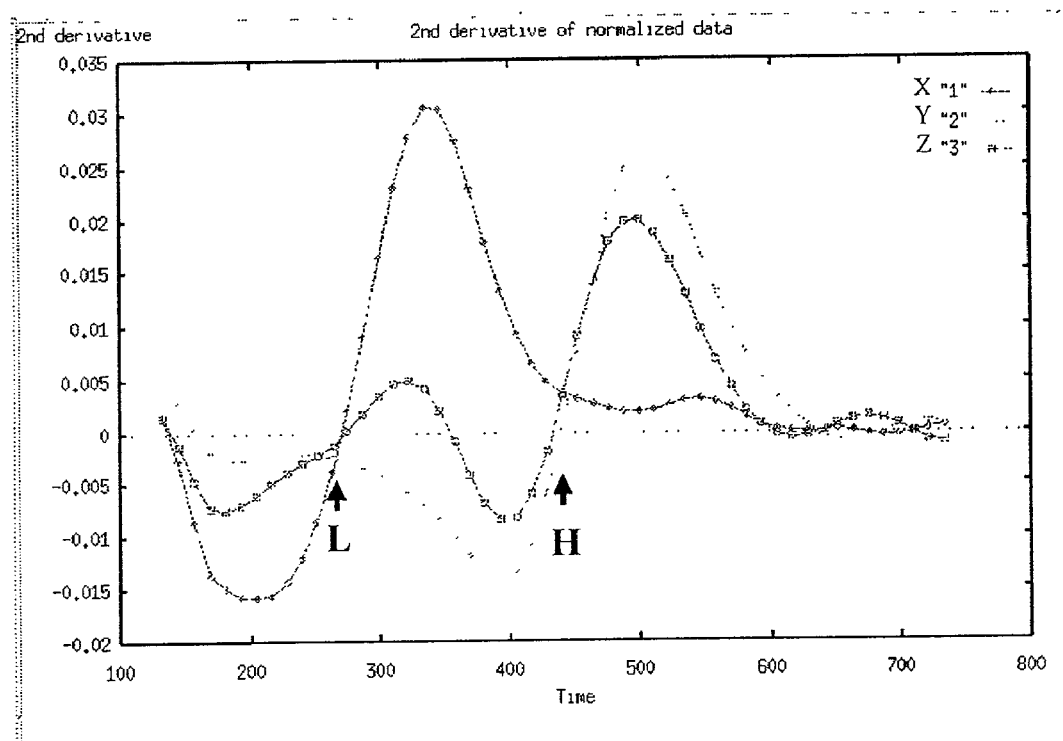

Figure 3.b.
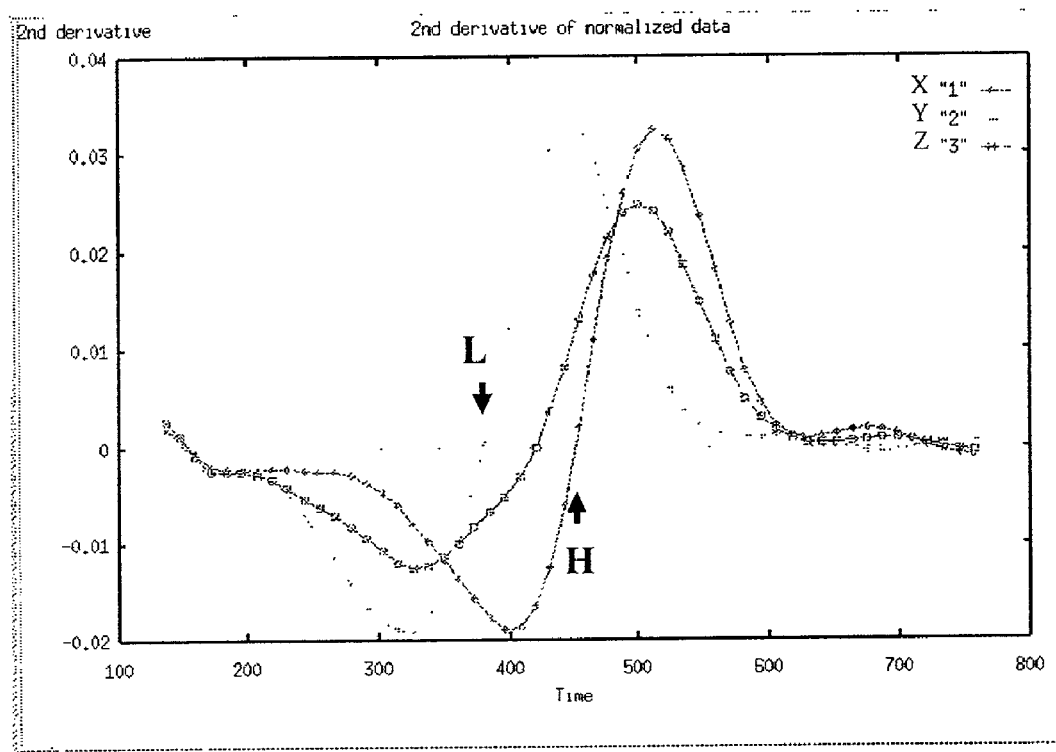

SEQUENCE LISTING

```
<160> NUMBER OF SEQ ID NOS: 5

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence:PRIMER

<400> SEQUENCE: 1
ctgcattttg gcacaaccca ccgtacaact gacaaacagg aatgaaac            48

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:PRIMER

<400> SEQUENCE: 2
ctgcattttg gcacaaccc                                            19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:PRIMER

<400> SEQUENCE: 3
gtttcattcc tgtttgtcag t                                         21

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence:PRIMER
```

-continued

```
<400> SEQUENCE: 4
agttgtacgg tgggt                                                        15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:PRIMER

<400> SEQUENCE: 5
agttgtatgg tgggt                                                        15
```

DETECTION OF NUCLEIC ACID POLYMORPHISM

CROSS-REFERENCE TO RELATED APPLICATIONS

This application is a continuation-in-part of International Application PCT/GB99/03329, filed Oct. 7, 1999, which claims priority to British application No. 9821989.2, filed on Oct. 8, 1998, both of which are incorporated by reference herein.

FIELD OF THE INVENTION

This disclosure concerns an invention relating generally to nucleic acid sequence variation and more specifically to the scoring of variants (polymorphisms and mutations) occurring in natural DNA sequences.

BACKGROUND OF THE INVENTION

In genomes of species such as the human it is estimated that on average 1 in $10^3$ nucleotides is variant between any two equivalent chromosomes. Although most such variations will be functionally neutral, a small proportion will underlie human phenotypic differences including the risk of disease. DNA variations may be investigated by determining the extent of hybridization of allele specific probes against DNA segments containing the locus of the variation. In this way, it is possible to record 'matches' (presence of DNA identical to the probe) and 'mis-matches' (presence of DNA non-identical to the probe) for DNA samples from individuals under investigation. However, a problem with existing methods of this type is that it is difficult to determine an adequately discriminatory hybridization stringency. An improved method of increased reliability and simplicity is therefore much needed.

SUMMARY OF THE INVENTION

The invention, which is defined by the claims set forth at the end of this document, is directed to methods and apparata which at least partially alleviate the aforementioned problems. A basic understanding of some of the preferred features of the invention can be attained from a review of the following brief summary of the invention, with more details being provided elsewhere in this document.

The present invention comprises a method of detecting DNA variation which comprises forming a complex consisting of:

(a) a single strand of a DNA sequence containing the locus of a variation, (b) an oligonucleotide or DNA analogue probe specific for one allele of the variation hybridized to the single strand (a) to form a duplex, and (c) a marker specific for the duplex structure of (a) plus (b) and which reacts uniquely when interacting within the duplex, (d) continually measuring an output signal of the extent of the resulting reaction of the marker and the duplex while steadily increasing the denaturing environment containing the complex, and recording the conditions at which a change in reaction output signal occurs (herein termed the denaturing point) which is attributable to dissociation of the complex and is thereby correlated with the strength with which the probe (b) has hybridized to the single strand (a).

In the assay as defined above the complex is first formed and then denaturing conditions are applied to determine the point at which the duplex dissociates. When heating is employed as the method of denaturing the duplex the reaction is carried out in the following way. The test sample is first cooled to hybridize the oligonucleotide or probe to the target DNA, and then heated steadily in a controlled and monitored fashion to detect the denaturing temperature. It will be appreciated, however, that the formation of duplex DNA is an equilibrium reaction, i.e. a two way reaction. It is therefore possible to reverse the order of the events described above. Thus all the defined components of the reaction can be brought together at raised temperature and then cooled in a similarly controlled and monitored fashion to detect the temperature at which the duplex (and complex) is formed. This may be described as the "annealing" temperature. This can be considered to be equivalent to the "denaturing" temperature, but will actually be a different value due to the complex chemistry involved. This principle of equivalence can of course be applied when denaturing/annealing conditions other than heating are employed for the purposes of the invention.

The method defined in the previous paragraph is one in which the components (a), (b) and (c) are brought together prior to formation of the defined complex and under conditions in which (a) and (b) do not hybridize, whereupon the conditions of their environment are steadily adjusted to cause formation of the duplex and resulting complex, and a reaction output signal is obtained indicative of the occurrence of hybridization of (a) and (b) (herein termed the annealing point).

More generally, therefore, the invention comprises a method of detecting DNA variation by monitoring the formation or dissociation of a complex consisting of:

(a) a single strand of a DNA sequence containing the locus of a variation, (b) an oligonucleotide or DNA analogue probe specific for one allele of the variation and capable of hybridizing to the single strand (a) to form a duplex, (c) a marker specific for the duplex structure of (a) plus (b) which forms a complex with the said duplex and reacts uniquely when interacting within the duplex, which comprises continually measuring an output signal indicative of interaction of the marker with duplex formed from the strand (a) and probe (b) and recording the conditions at which a change in reaction output signal occurs which is attributable to formation or dissociation of the complex and is thereby correlated with the strength with which the probe (b) has hybridized to the single strand (a).

The invention also comprises a method of detecting DNA variation which comprises bringing together:

(a) a single strand of a DNA sequence containing the locus of a variation, (b) an oligonucleotide or DNA analogue probe specific for one allele of the variation and capable of hybridizing to the single strand (a) to form a duplex, (c) a marker specific for the duplex structure of (a) plus (b) which forms a complex with the said duplex and reacts uniquely when interacting within the duplex, the components (a), (b) and (c) being brought together under conditions in which:

EITHER (i) the component (a) hybridizes to component (b) and the complex is formed with component (c)

OR (ii) the components (a) and (b) do not hybridize and the complex with component (c) is not formed, thereafter steadily and progressively adjusting the conditions of the environment, respectively, EITHER (i) to denature the formed duplex and cause dissociation of the complex, OR (ii) to cause formation of the duplex and resulting complex, and continually measuring an output signal indicative of the extent of hybridization of (a) and (b) and resulting complex formation with (c)

and recording the conditions in which a change of output signal occurs which is indicative of, respectively (i) dissociation of the complex or (ii) formation of the complex.

DNA duplexes can be denatured in a number of ways. The most usual systems employed are raised pH or increased temperature. Thus a controlled steady temperature increase is used to apply denaturing 'pressure' to the duplex, to examine at which point matched and mismatched duplexes denature. As an alternative a controlled steady pH increase can be used. Additionally, the principle of the invention may admit a DNA 'micro-chip' format (sub mm scale assay areas on flat surfaces—with the potential for mounting over electrical chips) in which case it opens the possibility of the use of increased negative electric charge (charge repulsion) to push the DNA strands (also negatively charged) away from the surface. If one partner of the duplex is surface bound, this effect will tend to denature the DNA, as for pH and temperature.

In order to choose alternative signal detection methods, any system that gives a different signal for double stranded and single stranded DNAs can be used as the basis for detecting the denaturing (or hybridizing) of the probe plus target DNA duplex. The most well known physico-chemical difference between double stranded and single stranded DNA is the spectrum of UV light absorption caused by these molecular species. Apparatus can be devised to utilize this parameter.

A preferred marker for use in the method defined above is one based on fluorescence. Where a fluorescent marker is used, the present invention comprises a method of detecting DNA variation which comprises forming a complex consisting of:

(a) a single strand of a DNA sequence containing the locus of a variation, (b) an oligonucleotide probe specific for one allele of the variation hybridized to the single strand (a) to form a duplex, and (c) a marker specific for the duplex form of (a) and (b) and which fluoresces when bound to or intercalated within the double stranded DNA, continually measuring the resulting fluorescence while steadily increasing the temperature of the environment containing the complex, and recording the temperature (herein termed the melting temperature) at which a decrease of fluorescence occurs which is attributable to dissociation of the complex and is thereby correlated with the strength with which the probe (b) has hybridized to the single strand (a).

Further advantages, features, and objects of the invention will be apparent from the following detailed description of the invention in conjunction with the associated drawings.

BRIEF DESCRIPTION OF THE DRAWINGS

FIG. 1b is a graph of primary DASH assay data showing the results for the 'T Probe';

FIG. 2a is a graph of negative $1^{st}$ derivative DASH assay data for an NDUFB4 gene polymorphism showing the results for the 'C Probe';

FIG. 2b is a graph of negative $1^{st}$ derivative DASH assay data for an NDUFB4 gene polymorphism showing the results for the 'T Probe';

FIG. 3a is a graph of second derivative DASH assay data for an NDUFB4 gene polymorphism showing the results for the 'C Probe';

FIG. 3b is a graph of second derivative DASH assay data for an NDUFB4 gene polymorphism showing the results for the 'T Probe';

DETAILED DESCRIPTION OF PREFERRED EMBODIMENTS OF THE INVENTION

Figure 4:
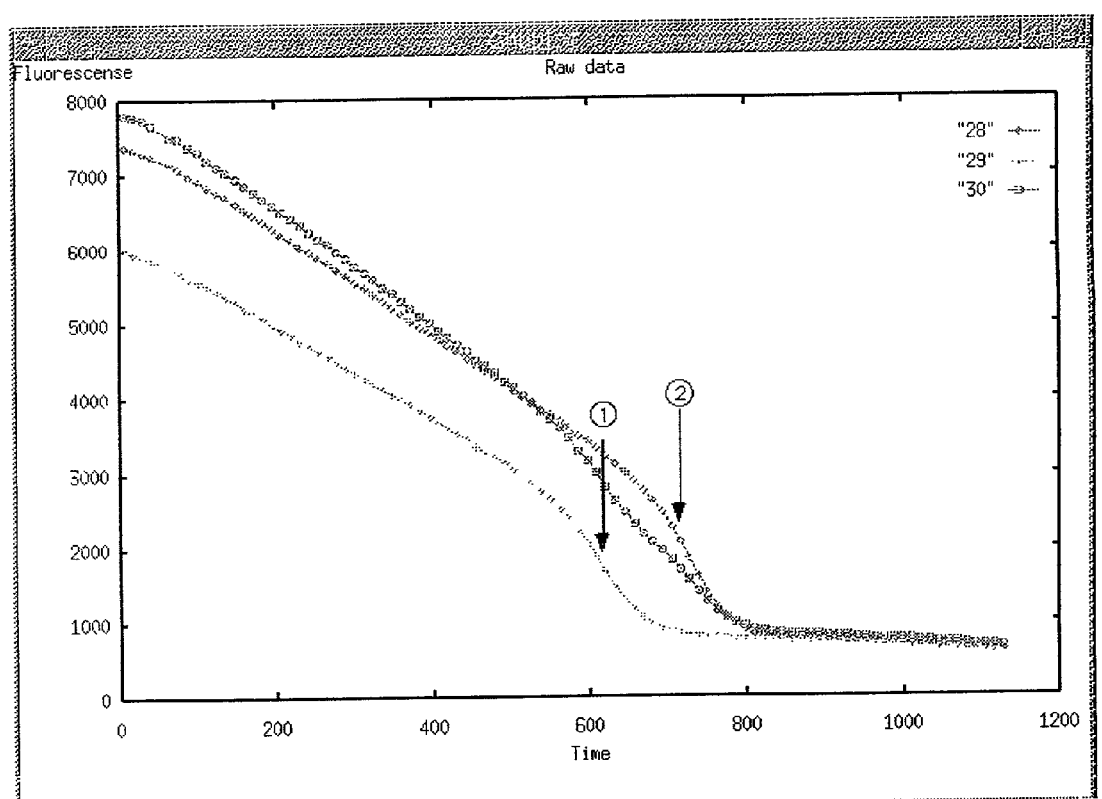
FIG. 4 is a graph of data for 3 different DNA samples assayed with one allele specific probe.

In carrying out methods in accordance with the type previously described, it will be usual to form a series of two or more complexes of the kind defined, each with a probe specific for a different allele of the variation, and observing their respective transition points so as to distinguish alleles of the variation plus the homozygous or heterozygous state if appropriate. Using fluorescence, the melting temperature is conveniently determined by reference to the negative or positive first or second derivative (differential) of the output signal (fluorescence measurement) curve.

The method of this invention is advantageously carried out with the single strand DNA attached to a support material, most conveniently by a biotin/streptavidin type interaction. The single strand is derived from a double stranded DNA product of PCR amplification of a target sequence. Low complexity sequences, such as cultured viral genomes, purified cloned DNAs etc., can be end-labelled with streptavidin or such and used without specific amplification. It is convenient to work with a PCR product over 100 base pairs or preferably from 40 to 100 base pairs in length. The complex may be formed by adding the probe and marker to the single strand in an appropriate buffer solution.

As indicated above, the assay may be performed with the target DNA bound to a surface. However, the invention is not limited to any one format. Having both target and probe in free solution is also possible. There is also the option of localizing both to some shared region. Since the method involves forming a duplex between the two species, if neither or only one is localized, then one has to rely upon diffusion to bring the molecules together. However, by localizing the species in mutual close proximity (e.g. both to a surface, or even joining the two together at their ends) the efficiency of the duplex formation can be increased. This is of particular importance if hybridization is used as the basis of the assay rather than denaturation. It will also improve the speed of the initial hybridization for the denaturation based format. We have applied this for directly linked target and probe sequences i.e., one joined to the end of the other with a 'stuffer' sequence of irrelevant DNA between them to constitute a 'hinge'.

The method of the present invention it is not restricted to the use of single oligonucleotide probes. Additional probes can be used which anneal sequentially along the target DNA sequence. These might or might not be placed immediately contiguous i.e., with no gaps. Contiguously located probes will co-stabilize each other by the chemistry of 'base stacking' which is a well established phenomenon. It is also possible to construct a direct physical link between the adjacent probes. All the extra duplex DNA resulting from these extra probes increases the signal level of the assay.

1. Principle of the Method

The method of the invention, termed Dynamic Allele Specific Hybridization (DASH) is a technique that detects and scores single nucleotide differences in DNA sequences. In this assay, one strand of a double stranded DNA (e.g., a PCR product) is bound to a solid surface, and the other strand is removed. An oligonucleotide probe, specific for one version of the variation (an allele), is allowed to hybridize to the bound single strand. Next, an intercalating dye is added which fluoresces specifically in the presence of double stranded DNA (i.e., the oligonucleotide probe hybridized to the DNA sample). The reaction is now heated at a steady rate through a range of temperatures, while continually measuring fluorescence. As the temperature rises, the fluorescence decreases gradually until a temperature is reached where the oligonucleotide probe dissociates from the target DNA. This temperature is known as the melting temperature, or Tm. At this point, there is a rapid decrease in fluorescence.

DNA variations can have two or more alleles. To determine which alleles are present in a given DNA sample, an allele specific probe for each version of the variation may be assayed against the DNA sample. By comparing the 1st derivative of the fluorescence data from the two probings, it is possible to determine whether one or both alleles are present in the DNA sample.

2. Methodology

In outline form, the method consists of the following:
1. PCR amplification of the test DNA sequence
2. Binding one strand of the PCR product to a surface
3. Elution of unbound DNAs and PCR components
4. Neutralization of pH
5. Hybridization of an Allele Specific Oligonucleotide
6. Removal of excess Allele Specific Oligonucleotide
7. Detection of fluorescence during a heating regime
(7a. Repetition of steps 4–7 for alternative allele probes)
8. Analysis of fluorescence outputs 2.1. PCR Amplification To test genomic DNA, Polymerase Chain Reaction (PCR) is used to amplify a segment of DNA containing a known variation. Ideal conditions involve amplifying a short PCR fragment (from 40–100 bp), with 18–30 nucleotide long primers. One primer is biotinylated at its 5' end, allowing binding to a solid surface in a later step. Taq Gold, or other "Hot Start" type PCR conditions are used to limit primer dimer artifacts as much as possible. Effective PCR buffer conditions are as follows, with cycle times and numbers appropriate for the particular DNA fragment in question:

| | |
|---|---|
| Primer 1 (non-biotinylated) | 100 ng |
| Primer 2 (biotinylated) | 50 ng |

-continued

| | |
|---|---|
| DMSO | 5% |
| Nucleotides | 5.0 nmoles each dNTP |
| PCR Buffer | to 1× |
| Enzyme (e.g. Taq Gold) | 0.75 units |
| Water to a total volume: | 25 µl |

To limit the amount of non-incorporated biotinylated primer (which competes for binding sites on the solid surface), it was determined that 20 ng of biotinylated primer is sufficient. With a ratio of 20 ng biotinylated primer to 100 ng of non-biotinylated primer, the PCR product formation is still efficient, and the lower concentration of biotinylated primer decreases competition for streptavidin sites when binding to the solid surface.

PCR products of longer lengths (over 100 base pairs) work also, but there are some considerations. With longer PCR products, the variation should be located towards the biotinylated primer as there will be less kinetic motion at this end. Secondary structures can inhibit efficient binding of the probe and should be avoided. Also, the binding efficiency of long PCR products to the plates is reduced, presumably associated with secondary structure complications, as well as slower kinetics of molecule diffusion.

Short PCR products (40–100 bp) are preferable for several reasons. Less primer dimer artifact is seen with short PCR products. In addition, the overall efficiency of PCR is often superior when amplifying short products. If the binding capacity of the solid surface can be increased sufficiently, multiplex PCRs can be considered for use in the DASH assay. The short PCRs assists both in the efficiency of the multiplex PCR, and in the binding to the surface.

2.2. Binding One Strand of the PCR Product to a Solid Surface

The current binding surface format used is a 96 well microtitre plate that has been coated with steptavidin (available from various manufacturers). The total volume (25 µl) from one PCR is placed at room temperature in a well of the streptavidin coated plate, along with 25 µl buffer I (see sections 2.2.1–2.2.3 for buffer descriptions). The PCR product then becomes physically attached to the plate via the biotin label on the PCR product binding to the Streptavidin coating on the plate. Binding is left to proceed for anywhere between 5 minutes to 24 hours. Since the binding is 90% complete within one hour, the maximum efficiency is usually achieved after 30 minutes to 2 hours. Typically, less than 20% of the PCR product becomes bound to the plate, even at maximum efficiency. The binding solution can thus be removed and placed in a second well, which will also be completely saturated.

It is important in this step, as with all the following steps, that there are no air bubbles in the reaction tubes (wells on the microtitre plate). Air bubbles interfere with reactions between the solution and the surface of the microtitre plate, and should be removed before each incubation step. This can be done with a pipette tip, or tapping the well with a finger. In addition, it is necessary to remove as much as possible of the volume of solutions from the reaction tubes between steps. The reaction tube should appear "empty" before proceeding to the next step, with no visible solution left in the bottom of the well.

2.2.1. Hepes Buffer (Buffer I)

Figure 7:
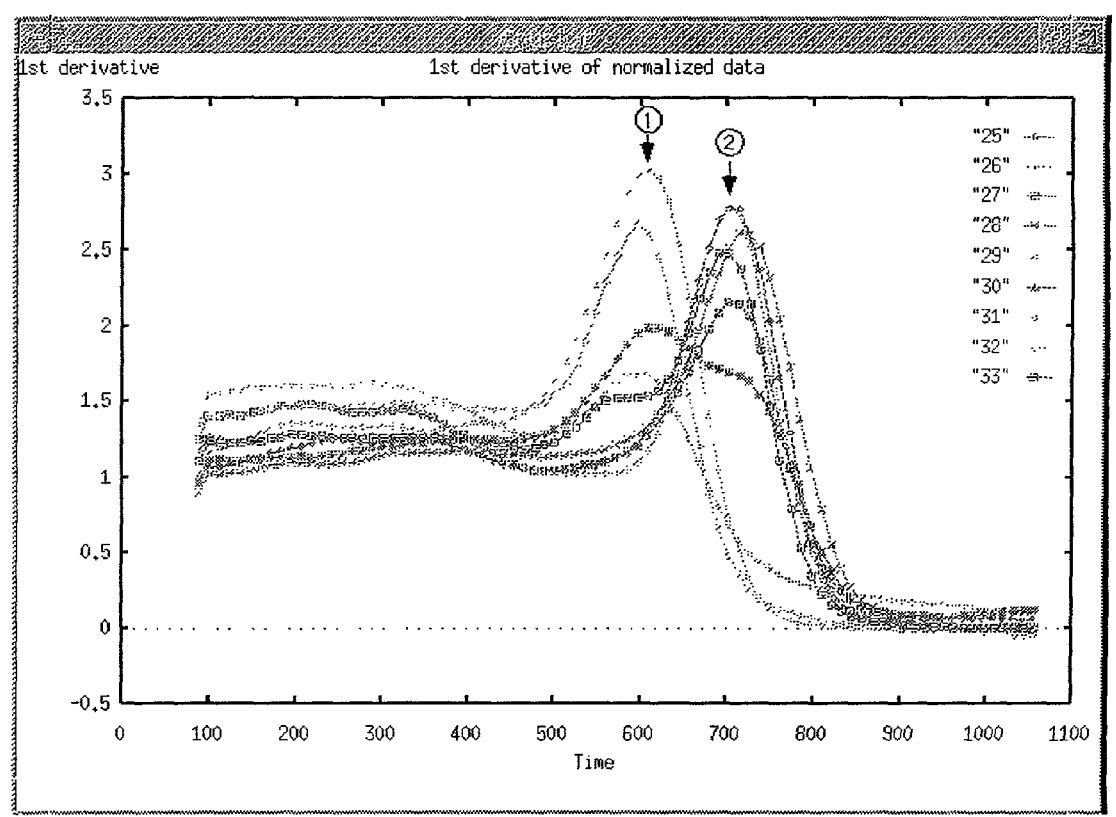
FIG. 7 is a graph of first derivative of normalized data for a plurality of DNA samples.

Buffer I consists of 100 mM Hepes, 50 mM NaCl, 10 mM EDTA, pH 7.8. There is an important reason why this buffer was chosen. It tends to dramatically standardize/normalize Tms based on the oligonucleotide length, regardless of G+C content. For example see the data given for FIG. 7.1.4. Many other buffers allow sufficient allele discrimination, however the absolute Tm's observed will vary greatly depending upon the G+C content.

2.2.2. Alternative Buffers & pH

SSPE, SSC, TEN, TES, MES, and Phosphate buffers were tested, and all maintained the integrity of the experiment. The different buffers vary the observed Tms of oligonucleotide/target DNA duplexes. The relationship between the Tm's of the matched oligo probe to a DNA target compared to the mismatched oligo hybridized to a target remained fairly constant at ~8–10° C. The above buffers supported a pH range from 6.0 to 9.8. There were no significant pH affects detected in this range. Below pH 6.0, the DNA analyzed tended to degrade, and at pH 10.0 and above the Tm was decreased to close to room temperature, preventing effective fluorescence measurement.

2.2.3. Buffer/Salt Concentrations

For the above buffers, a range of buffer and NaCl concentrations (1 mM to 400 mM) have been tested. At low salt concentrations, the observed Tm decreased as the buffer concentration increased. For example, in Hepes buffer at concentrations 1, 10, 40, and 100 mM with 0.0 M NaCl, the Tm values decreased from 88° C., 84° C., 78° C., and 72° C. respectively in one experiment.

At NaCl concentrations above 10 mM, the salt concentration rather than the buffer concentration becomes the major factor affecting the Tm values. Like buffer concentration, increasing NaCl concentration has the tendency to decrease the Tm. A range of NaCl concentrations were tested from 1 mM to 800 mM. At concentrations above 200 mM, the data becomes difficult to interpret (the curves were marked by random fluctuations).

2.2.4. Plastic-Ware

The microtitre plates and tubes employed must be made from fluorescence free plastic, and thus provide no additional background to the assay. The microtitre plates and tubes are also frosted to eliminate any fluorescence that may be detected from the outside of the tube. Thus, the plate and caps offer virtually no background to the experiment. Almost all background fluorescence is accounted for by the physical apparatus (excitation/detection equipment).

2.3. Elution of Second Strand of the PCR Product

Once the PCR product has bound to the plate, the non-bound PCR reagents are aspirated away, and 50 μl of NaOH solution is added. This denatures the PCR product, leaving single stranded DNA attached to the plate via the biotin/streptavidin interaction. 0.05 M NaOH was determined to be the minimum concentration of NaOH needed to reliably denature the double stranded PCR product, however 0.1 M allows room for concentration inaccuracies, and does not interfere with subsequent reactions. We allow 0.5–5.0 minutes for full denaturation of the PCR product in 0.1 M NaOH. Longer times are not necessary, but have no deleterious effects. The elution solution is aspirated away to remove all residual PCR components (non-incorporated primers, nucleotides, the enzyme, etc.), as well as the non-biotinylated PCR product strand.

2.4. Neutralization of pH

A solution of buffer I is prepared including a fluorescent dye specific for double stranded DNA. We currently use 'SYBR Green I' dye. The optimal concentration of this dye in the DASH assay is 1:10,000. Slight variations in dye concentrations do not affect the results. However, there are some characteristics of the SYBR Green I dye that should be noted (see sections 2.7.2., 3.1. and 3.2.). 50 μl of the Buffer I/dye solution is then added to the reaction tube. This buffer will both neutralize any remaining NaOH, and serve as the hybridization buffer in the next step. There should be minimal delay time before proceeding to the next step to minimize the opportunity for formation of secondary structures in the test DNA molecules.

2.5. Hybridization of an Allele Specific Oligonucleotide Probe

The SYBR Green I dye is included in the hybridization solution of the last step as it stabilizes the interaction between the oligonucleotide probe and the test DNA. 30 pmols of oligonucleotide probe (in 1 μl volume) is added to the reaction tube. The probe can alternatively be added as part of the neutralization buffer. This amount of probe allows hybridization to be completed within seconds, therefore there is no practical minimum incubation time for this step. Optimal results are obtained by performing a heating plus cooling step (heating to greater than 50° C. and cooling steadily over ~15 minutes to room temperature), rinsing the wells clear of unbound probe, and re-filling with 50 μl of the Buffer I/dye solution. Lower amounts of probe necessitate longer incubation periods, while higher concentrations do not decrease the necessary time for annealing. For further probe details, see section 2.5.1.

2.5.1. Probe Design and Use

Probe lengths of 13–25 base pairs have been tested, on three different variant loci. Allele discrimination is possible at all these lengths, however the optimal probe length was determined to be 15 base pairs. The 13 mer probes denatured at temperatures close to room temperature, and were determined to be non-ideal for this technique. The 25 mer achieved high fluorescence intensity (as fluorescence is a function of double strand DNA length), but allele discrimination was minimized. The 15 mer probe allowed sufficient fluorescence intensity and high discrimination between alleles.

The position of the variation in the hybridization probe was also examined. With a 15 mer probe, it was determined that the variant position gives the best discrimination when located in the central third of the probe. For single base variations the variant position is best placed at the central position. If the variant position is moved two bases from the center, the assay is less discriminatory.

In order to rapidly hybridize the probe to its DNA target on the solid support, 30 pmols was determined to be effective. This necessitates removal of the probe before fluorescence detection. An alternative was tested involving much lower amounts of probe (1–5 pmol) for hybridization, and subsequent processing without removal of the excess probe. Although allele distinction was achieved, the fluorescence values were low and the results were highly variable. With a higher binding capacity on the plate, this strategy may prove effective, decreasing the number of steps involved in the assay.

2.6. Removal of Excess Probe

The hybridization solution is next aspirated away to remove unhybridized probe molecules, and 50 μl of the buffer I/dye is added. The experiment is then ready for heating and fluorescence detection.

2.7. Fluorescence Detection and Heating Regime

The microtitre plate is placed in a heater/detector apparatus. Several devices are available which allow coincident temperature modulation and fluorescence detection as required to produce melting temperature profiles. These include a purpose-built "DASH machine" from Hybaid which allows automated scoring of alleles, and the Perkin-Elmer 7700 (Taqman) machine which was used for generation of the data presented in this document. The sample plate is heated from ~25° C. to ~90° C., while continually monitoring fluorescence. Most samples denature around 65° C.±10° C. Heating rates may vary at least between 0.01 to 1.0° C. per second with little loss of allele discrimination. We typically run assays at a rate of 0.1° C. per second. For details regarding the hardware of the Taqman device see section 2.7.1.

2.7.1. Perkin Elmer 7700 (Taqman) Sequence Detector

The detection device must detect the emission spectra given off by the double strand DNA specific fluorescent dye and keep track of the temperature at which the fluorescence data points were extracted. The excitation light source frequency must correspond to the requirements of the dye used in the DASH assay. For example, for dyes such as SYBR Green I excited near the 488 nm frequency, an Argon laser or a halogen lamp (filtered for the 488 nm frequency) is sufficient to excite the dye molecules. The Taqman is equipped with an argon laser that excites the fluorescent molecules. A filter is in place, removing all other wavelengths in the argon laser spectra, except for the 488 nm wave length.

The CCD camera on the Taqman detects a frequency range between 500 and 660 nm. The fluorescent signals are recorded into 5 nm "bins". Thus "bin1" would contain the fluorescence data from 500–505 nm. With the current arrangement, the light frequency range we use for the DASH assay is bin9 (545–550 nm), though this is not the only bin that is effective.

2.7.2. Fluorescent Dye

The dye employed must have a specificity such that its fluorescence in the presence of double stranded DNA is at least 10 times greater than when in free solution. We currently use 'SYBR Green I' dye which has a specific signal increase of ~1000 fold.

The optimal concentration of SYBR Green I dye depends directly on the amount of DNA present in the sample. We refer to this as the 'SYBR Green effect'. If the amount of dye used is below or above the optimal concentration for the given amount of DNA, the overall fluorescence observed in the assay will be reduced. For this assay, the optimal dye dilution is 1:10,000.

Alternative dyes have also been tested, and Vistra Green (Amersham) appears to have near identical properties to SYBR Green I, and could be used as an alternative dye for the DASH assay. Other dyes, such as acridinium orange and ethidium bromide gave high background fluorescence and are therefore not suitable for DASH. Other dyes, such as Yo-Pro I and To-Pro I have not been assayed due to the inappropriate light source plus filter combination in the Taqman device.

2.7.3. Assay Solution Additives

An array of different additives were screened for effects on the assay. Common destabilizing agents, like formamide, were screened and shown to be non-beneficial to the assay. In addition, hybridization reagents like Tetra-methyl Ammonium Chloride (TMAC), Bovine Serum Albumin (BSA), and Dextran Sulphate were tested, and again found to cause irregularities in the assay. Ionic detergents, even in trace amounts, destroyed the fluorescent signal completely. Non-ionic detergent showed no negative effects, except for the tendency to produce bubbles in the reaction tubes. With non-ionic detergents, much more care was needed to make sure bubbles did not remain in the reaction tubes at the various steps in the DASH assay. Dimethyl Sulfoxide was the only additive that was found to be beneficial, in that it can be added at a 50% level or less to decrease the observed Tm values.

2.8. Analysis of Fluorescence Outputs

Interpretation of the output fluorescence versus temperature graphs is conveniently achieved as follows. A graph of the primary data is used to determine general information regarding how well the assay performed, i.e., the level of fluorescence and which samples may have failed. To score alleles, the results of a series of samples (different DNAs hybridized with the same allele specific probe) are plotted together according to the negative of the first derivative of the fluorescence values. For convenience, DNAs of known genotypes can be included in the series. For two alleles, two distinct peaks should be observed on the graph. These peaks correspond to maximal rates of fluorescence decrease (denaturing probe/target duplexes) in the primary data. The two peaks thus correspond to the Tms of the probe/target "matched" and "mismatched" duplexes.

The Tm peaks will be separated by at least 8° C. The higher temperature Tm peak indicates the presence in a given DNA sample of the sequence corresponding to the allele specific probe used in the experiment. This can be termed a 'match', as the allele specific probe matches perfectly to molecules in the test DNA. The lower temperature Tm peak indicates a 'mismatch', i.e., the presence of hybridizing sequences in the test DNA that are similar but non-perfectly matched to the allele specific probe used in the experiment. For the typical case of a two allele system, this 'mismatch' will be the allele not represented by the probes' sequence. Often a single sample will give both peaks, indicating that it is heterozygous for the two tested alleles.

The bound DNA samples may be reprocessed through steps 4–7 of the procedure using a probe comprising the second (or several subsequent) allele sequence(s), and the data is analyzed as above. By comparing the two sets of data, it is possible to determine with high reliability which alleles are present in the DNA samples. If a DNA sample scores a 'match' with the probe specific to allele 1, and a 'mismatch' with the probe specific to allele 2, the DNA sample is scored 'homozygous allele 1'. If the DNA sample scores a 'mismatch' with allele 1, and a 'match' with the allele 2 probe, then the sample is scored 'homozygous allele 2'. If the DNA sample is scored a 'match' for both alleles, then the sample is scored 'heterozygous for alleles 1 and 2'. For examples of primary data, 1st derivative, and 2nd derivative graphs, see section 7.1.

3. Novel Discoveries 3.1. Melting Temperature (Tm)

In this assay, the temperature at which the oligonucleotide probe disassociates from the DNA target is determined by interactions between the dye, the buffer, and the salt concentrations. SYBR Green I dye stabilizes the probe/DNA duplex structure, raising the Tm with increases in Dye concentration. Increasing Salt and Buffer concentrations decrease the Tm, presumably by decreasing the potential of the dye to bind (and so stabilize) the duplex DNA structure.

3.2. Dye Effects

SYBR Green I intercalates into double stranded DNA structures and thereby increases the Tm distinction between matched and mismatched duplexes. The Tm difference between a completely 15mer oligonucleotide probe hybridized to it's perfectly matched DNA target compared to a target mismatched at the central position is roughly 8° C. The expected difference based on melting temperature calculations for normal DNA solutions would be around 2–3°

C. (depending on the DNA nucleotide sequence of the probe). The current DASH format thus optimizes the potential for allele discrimination.

SYBR Green I also produces an effect wherein fluorescence is dependent on the double stranded DNA concentration and the concentration of the dye. Thus, for a constant DNA concentration, titrating SYBR Green Dye levels increases the fluorescence signal until a point is reached whereafter the fluorescence signal will decrease. We call this the 'SYBR Green Effect'. The concentration of dye used in this assay (1:10,000 dilution) is optimal for the amount of DNA that can be bound to the typical microtiter plate wells at this time.

3.3. Hepes Buffer

Hepes, as the base in the hybridization buffer, has some unique characteristics in this assay. In this buffer and dye combination, the Tm of the probe/target DNA complex is a function almost solely of the length of the probe. Variations in the DNA sequence context, or the G+C content, will not alter the observed Tm. This is of extreme importance for robustness of the DASH assay.

3.4. Dimethyl Sulfoxide (DMSO)

DMSO can be added to the hybridization buffer to lower the Tm of the oligonucleotide probe/target DNA complex without compromising the integrity of the assay. The sole affect is to lower the Tm of both allele Tm's without affecting the Tm difference between them.

3.5. Ionic Detergents

Use of ionic detergents, such as Sodium Dodecyl Sulphate, as low as 0.1% concentration, will completely destroy the fluorescent signal, presumably by interacting with the dye.

4. DASH Assay Components

4.1. Dyes

SYBR Green I Dye from Molecular Probes.

4.2. Plates

Microtitre plates from various suppliers. Micro Amp Optical plates, caps, and tubes from Perkin Elmer are designed especially for fluorometric measurements.

4.3. Oligonucleotides

PCR primers and allele specific oligonucleotide probes from Interactiva Biotechnologie, all HPLC purified in order to ensure maximal quality.

4.4. Fluorescence Monitoring Device

The Hybaid DASH system (Hybaid Limited, UK); ABI 7700 (Perkin Elmer; used in assays presented) or other detection temperature controlled device.

4.5. Buffers

All the components of buffers were from Sigma.

4.6. Software

The software developed to analyze the raw data, first derivative, and second derivatives of sample data was written by Kin-Chun Wong (Uppsala).

5. An Alternative Assay Format

An alternate format of binding the oligonucleotide probe to the plate followed by hybridization of the PCR product should be possible, but several technical problems arose with this design when tried. First is the problem of hybridizing the double stranded PCR product to the bound probe. Simple heat denaturation of the PCR product followed by cooling in the probe coated assay wells is insufficient. Presumably this is because of displacement reactions, i.e., the PCR product reforms it's double strand and displaces any probe hybridized to the target sequence.

To eliminate the complications caused by displacement reactions, we attempted to generate single stranded DNA from the PCR product for hybridization. For this we used unequal amounts of the two primers in the PCR, thus theoretically producing an excess of one strand of the PCR product (asymmetric PCR). This did improve the assay, but only to a small degree. Importantly, optimal PCR conditions varied compromising the robustness of the DASH assay.

The long length of the PCR products in free solution also presents a problem. This could slow reaction kinetics, and potential secondary structures would interfere with the hybridization reaction. In addition, once the long molecule is hybridized to the short fixed probe, there appears to be premature disassociation of the DNA/probe complex as thermal energy is added. In this format, it was found to be impossible to distinguish between alleles because all fluorescence signal is lost at very low temperatures. This is probably due to the hybridized PCR fragment having long non-hybridized tails sticking out into the solution. As the temperature rises, the long molecules will be pulled off by the solution kinetics rather than denatured according to Tm properties of the hybridized duplex.

Optimization of the probe bound format will require further experimentation, involving PCR conditions, buffer components, annealing strategies, as well as other parameters. The problems concerning production of single stranded DNA molecules for hybridization, and the kinetic considerations are avoided by using the DNA molecule bound format. The non-biotinylated strand is simply eluted away for single strand DNA production, and the kinetic limitations involving premature displacement are not observed.

6. Worked Example of DASH Analysis: Detection of Allelic Versions of a Bi-Allelic Single Nucleotide Polymorphism in the Human NDUFB4 Gene A DASH experiment was performed on a single nucleotide polymorphism in the human NDUFB4 gene which is located on an autosome. This is illustrated in FIG. 1 as 'DNA sequence 1' and it comprises a bi-allelism between 'A' and 'G' nucleotides. Three human genomic DNA samples, X, Y and Z, were employed that were known from earlier sequence analysis to be homozygous for the 'A' allele, homozygous for the 'G' allele, and heterozygous for these alleles, respectively.

6.1. Polymerase Chain Reaction (PCR)

PCR was performed on 50 ng aliquots of DNA samples X, Y and Z, using the PCR primers presented FIG. 1 as 'DNA Sequence 2' and 'DNA Sequence 3'. Reaction conditions were as follows; 25 ml total volume comprising 20 ng 'DNA Sequence 2' primer, 100 ng 'DNA Sequence 3' primer, 0.75u AmpliTaq-Gold polymerase (Perkin-Elmer), 10% dimethylsulphoxide, 1× Perkin-Elmer PCR-buffer (including 1.5 mM $MgCl_2$) and 0.2 mM each of dGTP, dATP, dTTP and dCTP. Thermal cycling employed a TouchDown™ Temperature Cycling Device (Hybaid Ltd) and the following cycle conditions: 1× (10 minutes at 94° C., 30 seconds at 50° C., 30 seconds at 72° C.), 17× (15 seconds at 94° C., 30 seconds at 50° C., 30 seconds at 72° C.), 18× (15 seconds at 94° C., 30 seconds at 50° C., 1 minute at 72° C.). This produced 48 base pair long PCR products that spanned the polymorphic locus and possessed a biotin moiety on the 5' end of one DNA strand.

6.2. Binding PCR Products to a Microtiter Plate

PCR reaction products were mixed with an equal volume of Buffer I (100 mM Hepes, 50 mM NaCl, 10 mM EDTA, pH 7.8) and transferred to individual wells of a streptavidin coated thin wall microtiter plate (Boehringer Mannheim). This was left at room temperature for 1 hour.

6.3. Elution of

All liquid volume (containing non-bound DNAs and other reagents) was thoroughly aspirated from the microtiter plate. Without delay, the wells were refilled with 50 ml 0.1M NaOH and left at room temperature for 5 minutes. The NaOH solution including the non-biotinylated DNA strand (now denatured from the bound strand) was then thoroughly removed.

6.4. Neutralization of Reaction Sample

Without delay, the wells were refilled with 50 ml Buffer I including SYBR Green I dye (1:10,000 fold dilution).

6.5. Hybridization of the First Allele Specific Oligonucleotide Probe 30 pmol of 'T Probe' (presented FIG. 1 as 'DNA Sequence 4') was added to each well in a volume of 1 ml water. Optical caps (Perkin Elmer) were used to seal each well, and the plate and its contents were heated to 60° C. and cooled steadily over ~15 minutes to room temperature. This was achieved upon a TouchDown™ Temperature Cycling Device (Hybaid Ltd).

6.6. Removal of Unbound Probe

The optical caps were removed, and all liquid volume was thoroughly aspirated from the microtiter plate. The wells were then refilled with 50 µl of Buffer I including SYBR Green I dye (1:10,000 fold dilution), and the optical caps were replaced.

6.7. Signal Detection Procedure

The microtitre plate was placed into a Perkin Elmer 7700 (Taqman) device, and a heating phase applied involving traversing from 35° C. to 80° C. at a steady rate of 0.1° C. per second. During this heating phase, the Taqman device repeatedly excited the samples with an argon laser light source (filtered at 488 nm) and collected the fluorescence that was emitted at a frequency range of 545–550 nm. Data points were collected at 7 second intervals for every well.

6.8. Reprobing with a Second Allele Specific Probe

Steps 3–8 above were repeated, this time replacing the 'T Probe' used in step 5 with the 'C Probe'(presented FIG. 1 as 'DNA Sequence 5').

6.9. Data Analysis and Interpretation of Results

Primary data was plotted on a fluorescence data versus time graph for all wells and for both probe interrogations. This data was 'smoothed' by plotting average fluorescence values determined from a sliding window of 8 data points. The resulting 'primary' data is shown in FIGS. 2*a* and 2*b*. A negative differential (derivative) curve of this graph was then plotted and this is shown in FIGS. 3*a* and 3*b*. A differential curve of the negative first differential curve was then plotted to give the second derivative shown in FIGS. 4*a* and 4*b*.

In FIGS. 3*a* and 3*b*, high (H) and low (L) temperature peaks can be seen indicating points of maximal rate of denaturation. These represent DASH signals for matched and one-base mismatched probe-target DNA duplexes respectively. In the second differential (FIG. 4) these points can be inferred from the points at which the curves cross the X axis. They are also visible in the primary data (FIG. 2), but can be hard to discern in this representation of DASH results.

Samples X and Y are seen to have only one matched (high temperature) peak in one negative first differential graph and only one mismatched (low temperature) peak in the other negative first differential graph. This indicates that they are homozygous samples. The probing during which X and Y gave a high temperature (matched) peak indicates which allele they contain. Thus, since X gave a high temperature peak with the 'T Probe', it is an 'A' allele homozygote. Conversely, Y gave a high temperature peak with the 'C Probe', and so is a 'G' allele homozygote.

Sample Z behaved differently to samples X and Y. It gave both high and low temperature peaks with the 'C Probe', and high and low temperature peaks (merged due to proximity into a single wide peak) with the 'T Probe'. Thus, this DNA sample must have both probe allele complementary sequences present within it. Hence it can be deduced to be a heterozygous sample containing both the 'A' and the 'G' alleles.

FIG. 1 shows DNA sequences for use in a DASH assay for scoring alleles of a human NDUFB4 gene polymorphism.

DNA Sequence 1 (Sequence listing SE1)

5': CTGCATTTTGGCACAACCCACC(G/A)TACAACT-GACAAACAGGAATGAAAC :3'

This is a 48 base pair genomic DNA sequence representing a portion of the human NDUFB4 gene. A bi-allelic single nucleotide polymorphism (G to A) is shown in parentheses towards the center of the sequence.

DNA Sequence 2 (Sequence listing SE2)

5': (Biotin)-CTGCATTTTGGCACAACCC:3'

This is a 19 base oligonucleotide sequence designed for use as 'PCR Primer 1' in a DASH assay for detection of alleles of the polymorphism shown in DNA sequence 1. It carries a biotin moiety attached to the 5' end.

DNA Sequence 3 (Sequence listing SE3)

5': GTTTCATTCCTGTTTGTCAGT:3'

This is a 21 base oligonucleotide sequence designed for use as 'PCR Primer 2' in a DASH assay for detection of alleles of the polymorphism shown in DNA sequence 1.

DNA Sequence 4 (Sequence listing SE4)

5': AGTTGTACGGTGGGT:3'

This is a 15 base oligonucleotide sequence designed for use as the 'C Probe'in a DASH assay for detection of the 'G' allele of the polymorphism shown in DNA sequence 1.

DNA Sequence 5 (Sequence listing SE5)

5': AGTTGTATGGTGGGT:3'

This is a 15 base oligonucleotide sequence designed for use as the 'T Probe' in a DASH assay for detection of the 'A' allele of the polymorphism shown in DNA sequence 1.

FIGS. 1*a* and 1*b* show primary DASH assay data for an NDUFB4 gene polymorphism, in which 'H' and 'L' indicate points of maximum denaturation rates for matched and mismatched probe-target duplexes respectively. X, Y, and Z are the sample DNAs. FIG. 1*a* shows the results for the 'C Probe'while FIG. 1*b* shows the results for the 'T Probe'.

FIGS. 2*a* and 2*b* show negative 1st derivative DASH assay data for an NDUFB4 gene polymorphism, in which 'H' and 'L' indicate points of maximum denaturation rates for matched and mismatched probe-target duplexes respectively. X, Y, and Z are the sample DNAs. FIG. 2*a* shows the results for the 'C Probe'while FIG. 2*b* shows the results for the 'T Probe'.

FIGS. 3*a* and 3*b* show 2nd derivative DASH assay data for an NDUFB4 gene polymorphism, in which 'H' and 'L' indicate points of maximum denaturation rates for matched and mismatched probe-target duplexes respectively. X, Y, and Z are the sample DNAs. FIG. 3*a* shows the results for the 'C Probe'while FIG. 3*b* shows the results for the 'T Probe'.

7.1. Example Graphs

7.1.1. Primary Data

FIG. 4 shows data for 3 different DNA samples assayed with one allele specific probe. Samples "28, 29, and 30"

illustrate typical results for homozygous match, mismatch, and heterozygous samples respectively. Notice that the heterozygous sample 30 exhibits characteristics of both the match and mismatch curves. (1) Tm of mismatched probe/target duplex. (2) Tm of matched probe/target duplex.

7.1.2. Negative First derivative

Figure 5:
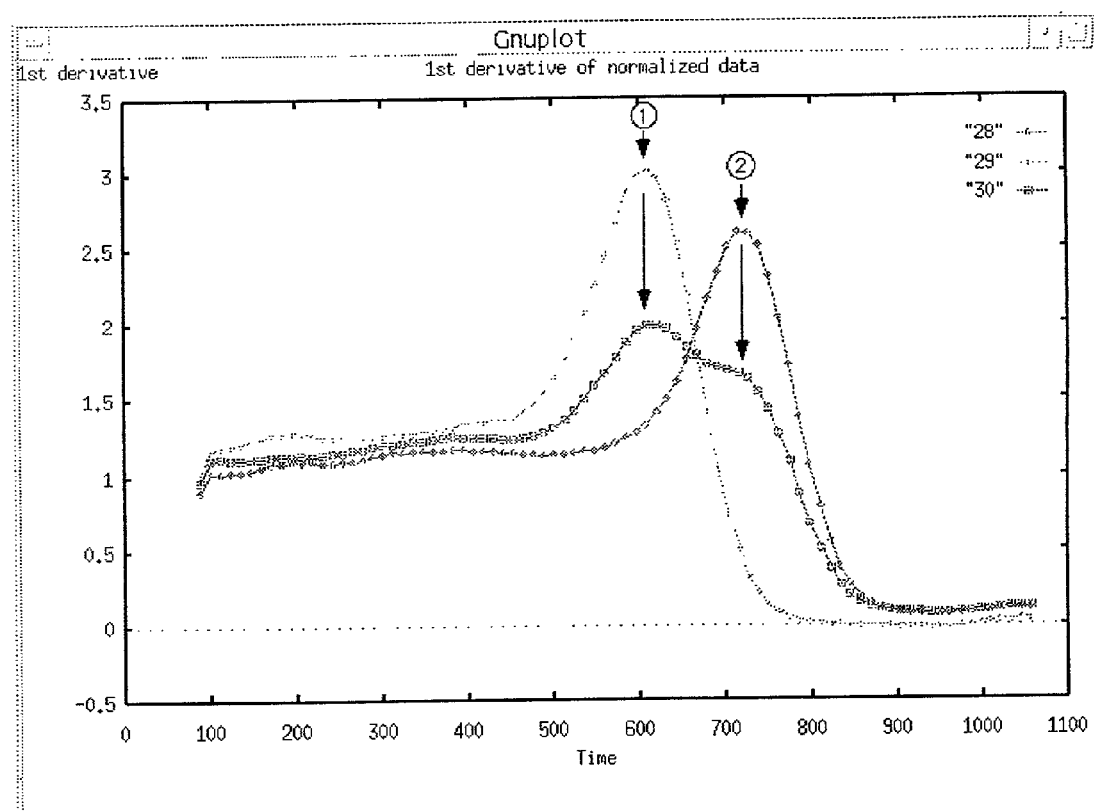
FIG. 5 is a graph of the negative first derivative of three DNA samples.

The negative first derivative of three DNA samples are shown in FIG. 5. The DNA samples are probed with one allele specific probe. Samples 28, 29, and 30 are homozygous match, homozygous mismatch, and heterozygous, respectively, for the probe allele. (1) Tm of mismatched probe/target duplex. (2) Tm of matched probe/target duplex.

7.1.3. Second Derivative

Figure 6:
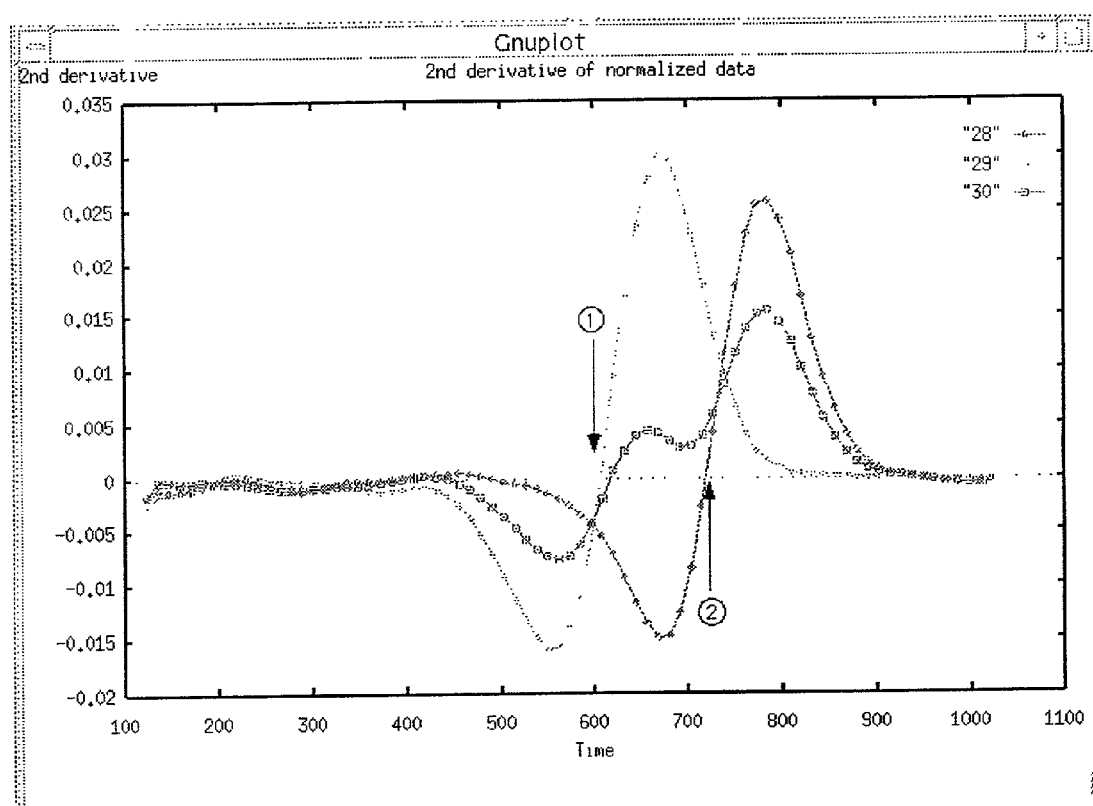
FIG. 6 is a graph of second derivative data for 3 DNA samples.

Second derivative data for 3 DNA samples is shown in FIG. 6. Samples 28, 29, and 30 are homozygous match, homozygous mismatch, and heterozygous. (1) Tm of mismatched probe/target duplex. (2) Tm of matched probe/target duplex.

7.1.4. Normalization of Tms by Hepes for three different variations

Samples 25–27, 28–30, and 31–33 are negative first derivative sets of data for three different variations. Each set was probed with a locus specific 15mer allele specific oligonucleotide probe corresponding to the respective variation being assayed. The G+C content of these probes varied from 40% to 70%. According to melting temperature theory the Tm's of the probe/target duplexes should vary between these different sequences, but the DASH assay conditions with Hepes buffer normalize the data to fixed Tm values. (1) Tm of mismatched probe/target duplex. (2) Tm of matched probe/target duplex.

Preferred DASH Operating System

The preferred embodiment provides an operating system for carrying out DASH experiments and for analyzing experimental results obtained thereby.

The preferred system is implemented on a computer of any suitable form, such as a personal computer. The hardware and software elements required to achieve the functions described below will be readily apparent to the person skilled in the art; therefore, the description which follows focuses only upon the various features of the operating system which provide advantageous analysis of experimental results and management of the experimental data.

The DASH machine provides a mechanism for obtaining melting curves and automated scoring of samples based upon the data analysis described below. As DNA hybrids melt (as a duplex of two DNA strands is destroyed), by monitoring the degree of melting (in a preferred embodiment by monitoring the loss of fluorescence) a sigmoidal curve is produced. Conversion of this curve to a negative first derivative converts the point of inflection of the curve to a peak. The peak identifies the "melting temperature" of the two-strand DNA complex (defined to the point at which 50% of the complex has been destroyed).

Separate but related techniques can be automatically scored by the peak detection software of the preferred system. The first is DASH, in which a short oligonucleotide DNA strand is hybridized over a known polymorphic DNA sequence. The melting temperature of a perfectly matched oligonucleotide differs from that of a mismatched oligonucleotide, thus defining the sequence. Another technique referred to as "McSNP" (explained below) can be assayed using the DASH machine and scored using peak detection software which uses identical scoring algorithms to the DASH scoring software.

The DASH software is designed automatically to score this peak, by defining the temperature at which the peak is found and determining whether this occurs within one of two zones (which define the areas within which are the melting temperatures of the matched or mismatched oligonucleotides). On this basis samples are automatically scored as homozygous for either matched or mismatched sequences, or as heterozygous (containing both possible variants).

The "McSNP" assay is based upon the standard molecular biology technique of Amplification Fragment Length Polymorphism (AFLP). In this technique a PCR fragment in which a possible DNA polymorphism exists is generated. The polymorphism must exist within a short sequence which is recognized by a DNA-cutting enzyme (restriction endonuclease). Incubation of the DNA with this enzyme will result in the single DNA molecule being cut at this site. Where the PCR fragment is generated from a DNA sequence having a different sequence at this cut site, the site will not be recognized and hence the DNA is not cut. In the standard AFLP technique, the DNA is size fractionated to define whether cutting has taken place. The McSNP assay uses melting temperatures of the cut or uncut fragments to define whether cutting has occurred. If the fragment has not been cut, a particular melting temperature peak representing the whole fragment (and therefore at a relatively high temperature) will be produced. Cutting of the fragment will result in two peaks representing the melting temperature of the resulting digestion products. In the case of the heterozygote, three peaks are produced. In general, both techniques allow the user to define the zones in which melting temperatures are expected and to define how samples will be scored based upon this data. Based upon the match, mismatch or both, peaks are detected (in DASH), or on the cut, uncut or both (in McSNP), the user can define how the software should automatically score the samples.

In each case, the means of detecting the peak value is identical, as is the means used to define whether the peak exists within a particular user-defined zone. The preferred embodiment is described with reference to DASH experiments.

Figures 8, 9:
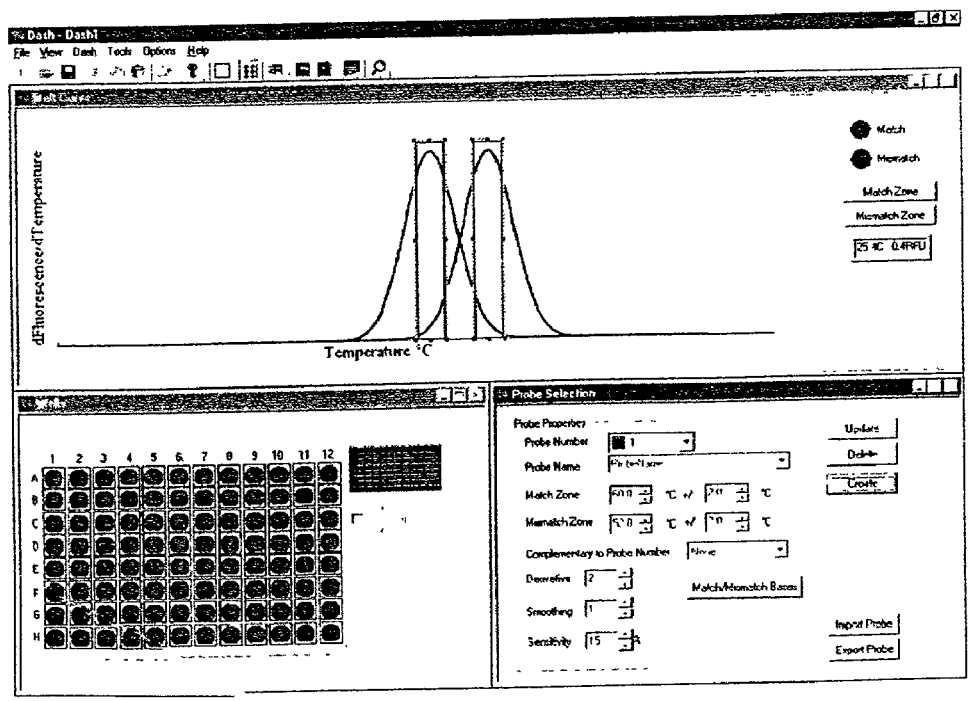
FIG. 8 is a view of an embodiment of database for storing the experimental results for an array of samples.
FIG. 9 is a view of a preferred embodiment of analysis scheme.

In the preferred embodiment, all data relating to an experiment is stored in a database within the operating system. FIG. 8 shows the preferred database format. This typically provides a series of records, with one record for each sample under test. For example, when the test is carried out on an array of 96 samples, the database will include records for each of the 96 samples, conveniently referenced by the sample well identifier. The database also includes fields giving the classification determined for the particular sample, the match and mismatch zones, the measured melting temperature and the quality of the sample.

In the embodiment shown in FIG. 8, the fields of the database are the following:

| FIELD | DATA ENTRY |
| --- | --- |
| Well Ref | A1:H12 (Automatic) |
| Sample Name | Up to 96 samples may be entered, either manually or by import from a previous database |
| Probe No. | Up to 96 probes can be defined (i.e. one per well). Entered automatically from entry into the Probe Selection Screen. |
| Probe Name | Character string. Entered automatically from entry into the Probe Selection Screen. |
| Classification | Homozygous Match, Homozygous Mismatch, Heterozygote, Empty Well/No Peaks Detected or Erroneous Data (when using complementary probing). Entered for automatically scored data. |

-continued

| FIELD | DATA ENTRY |
|---|---|
| Match Zone | Automatically generated co-ordinates derived from the Probe Classification Match Zone settings. |
| Mismatch Zone | Automatically generated co-ordinates derived from the Probe Classification Mismatch Zone settings. |
| Tm | If the software has detected a valid melting temperature peak it is displayed in the field. |
| Quality (%) | This is a quality percentage score indicating how reliable the software calculates the results to be. |
| (A)uto/(M)anual | A - results derived automatically.<br>M - Manually scored results, this appears if classification, match zone, mismatch zone or quality percentage is edited by the user. |

The preferred system is arranged such that a DASH experiment is carried out on all of the relevant samples and the results, in particular the melting temperature curve, are digitized and stored in the fields of the record relating to each sample tested. The database will contain all test details including also the settings of the apparatus, sample names and so on. The set-up automatically updates the database file when new data is available, for example from subsequent tests, and also allows the manual editing of the data in any field of the database.

Once the experimental data has been obtained and stored, the preferred system allows for analysis of this data to determine and classify the results of the experiment. Thus, the results from a single experiment can be used in a plurality of different analyses, thereby avoiding the need to repeat the experiment.

A first stage in the analysis procedure is described with reference to FIG. 9, which shows in the form of a display the system user interface for this stage of the analysis.

The display provides a window giving an indication of (in this example) the 96 sample wells, this indication changing appearance or color in dependence upon the state of the sample well. For example, if selected sample wells chosen for a particular analysis, they may initially be represented by a particular color, with sample wells not selected for analysis being shown in a different color to indicate to the user that they are inoperative at that point in time.

The other windows of the display show the melt curve for a selected one of the sample wells and a Probe Selection window. Probe selection window provides for entry of all data which is used to classify the experimental result (that is to score the DASH results). The window allows the user to select the match and mismatch zones within which the software looks for melting temperature peaks, defines the probe name and the wells which are probed (analyzed) with this probe. It also allows definition of the way in which data from the wells is smoothed. Smoothing is preferably based upon the setting of a threshold for the value of change in fluorescence over change in temperature, so as to remove from the results any changes which may be caused by extraneous effects, such as noise and the like.

The system is programmed to detect peaks in negative first derivative data (explained above). As will be apparent in FIG. 9, the Probe Selection window, with reference to the melt curve window, is used to define how the peaks are automatically scored, that is the zones in which a match or mismatch peak should occur. The match and mismatch zones are user settable to particular temperature ranges, with the example in FIG. 9 providing a match zone of 2° C. either side of a datum point of 60° C. and a mismatch zone 2° C. either side of a datum point 52° C. The width of each match and mismatch zone determines the sensitivity of determination of the peaks.

The Probe Selection window also allows for the entering of information relating to the probe names, reagents used to be stored for use in autoscoring by the system, melting temperatures (with peak width determination) for matched and mismatched oligos, and the wells to which these test parameters apply, as described below.

The selection of wells is preferably performed by selecting (for example by means of a moving cursor within the well window), individual wells to be tested with a particular selected probe or by "rubber banding" groups of wells by any suitable method. Upon selection of wells for a particular probe, a specific color is allocated to the wells for each particular probe to indicate their selection.

A plurality of such probes can be defined, to test different melting temperature peaks, with the system providing for the assignment of a specific probe number and/or specific probe name to each defined probe.

The specific embodiment shown in FIG. 9 provides several different ways in which the user can define the zone within which the software will search for a valid match or mismatch peak. These are as follows:

a) Direct entry of data into the Probe Selection screen. Direct entry of data may be by use of the graphical interface ("Melt Curve") of the melt curve window. To perform this function, the user can click on the icon representing the Match or Mismatch option at the right of the window. It will then be possible to click on the relevant zone (blue for the match zone, red for the mismatch zone), and move and stretch the defining box as desired. As changes are made to the position and size of the box, this will be reflected in the numbers entered in the relevant box in the Probe Selection window. Similarly, if this data is entered numerically, this will be reflected in the size and shape of the graphic base in the melt curve window.

b) Import/Export of Probe data. Where an experiment has been run using the same probe as in the current experiment, the data relating to this probe may be imported. This is done by first saving the probe data to a separate file by clicking on the "Export Probe" option in the Probe Selection window. A window will open, giving the option to save the probe data as a probe (.prb) file. Probe parameters saved in this way can subsequently be imported by clicking on the "Import Probe" option and selection of the desired file. Note that it may be desirable to run a plate using all of the same probes as used for a previous plate. This is most simply performed by opening the previous file and re-saving under an alternative name. If the sample names are different these can be replaced. The experiment can then be run with the parameters (heating rate, start/stop temperatures) altered if desired prior to clicking on the start button.

c) Entry of probe parameters using the Melt Curve within the Results screen. On completion of a DASH experiment in which new probes with undefined scoring parameters are used, it is useful to use the Melt Curve to allow definition. The DASH software allows use of the Melt Curves produced within the Results screen to position exactly the match and mismatch zones. It is necessary first to define probe names and assign the wells to which that probe will relate. Then, to set zones, with the cursor positioned within the Melt Curve window, a mouse button can be depressed to select the "Create Match Zone" (or "Create Mismatch Zone") option. A rectangle will appear within the graphic window, which can be sized and shaped by clicking and dragging in convention manner. Upon setting the zone to that required a click of a mouse button, preferably provides an "Assign Zone to Probe" option. The probes existing within this file will be presented as options for which the zone may be accepted. Selection of the desired probe will result in the data relating to the zone being entered automatically into the Probe Selection screen, and thereby assigned to the relevant wells. Upon selecting the Classify Results Data option, these will be scored accordingly. Note that only the X-axis is relevant in setting the zone, boxing of the curves being examined allows greater accuracy in setting the zone.

Complementary Probing within a Single Plate

Figure 12:
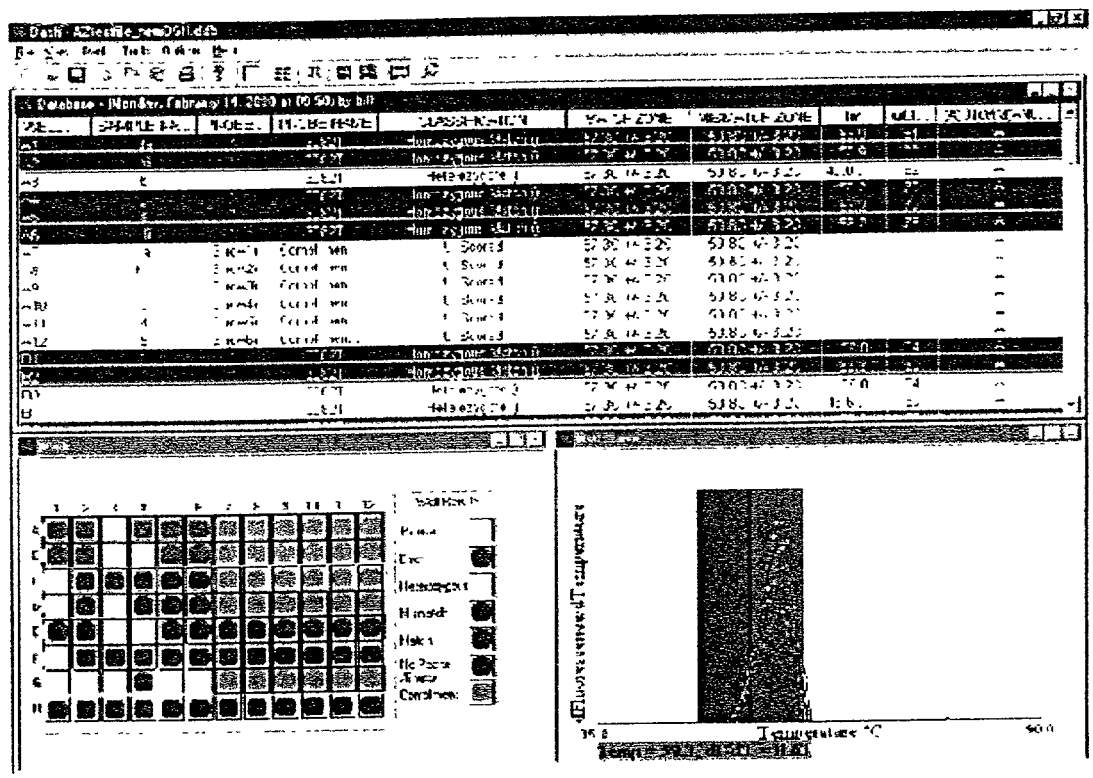
FIG. 12 is a view of a scheme for displaying and modifying analysis results.

The preferred system allows "complementary probing" which simply means that a given sample is probed with both possible matching probes to a given polymorphism. In this scenario for any given sample, one probe should match and the other mismatch (or, in the case of a heterozygous sample, each of the probes should both match and mismatch) the amplified DNA. Using the complementary probing option therefore gives greater certainty to the results obtained. For example, matching to both probes ("homozygous match" in both cases) will give an unacceptable result to which the user's attention will be drawn by an error being entered in the Results screen (FIG. 12).

If all samples are to be analyzed by complementary probing, the user has the option to select to use a complementary pattern, in which wells in one half of the plate (for example columns 7–12 for each row) are assigned as the complement to those on the other half of the plate (columns 1–6). The system automatically assigns the complementary wells in a symmetrical fashion (hence A7 is the complement to A1; A8 to A2; B7 to B1 etc).

It is also possible to use complementary probing by assigning one probe as being complementary to a second probe, using the box marked "complementary to probe number" in FIG. 9.

In order to use this option, there should be an equal number of each of the two probes on the test plate. If this is not the case, the software will decline entry of the complementary probing option.

Complementary Probing Using a Previous File

It is possible to re-probe immobilized DNA from a previous DASH experiment using a second probe. When this is done, the system allows comparison of data between plates of two experiments. Selecting the complementary option in this example will bring up a window allowing selection of a file from those DASH files currently stored. If the probes used in this plate are indeed set up such that complementary probing is possible, the plate will be scored and the newly scored file will be renamed with a "_comp" appended to indicate that scoring has been performed as complementary to a previous experiment. All of the usual DASH scoring and data transfer functions can be used within this file. Thereafter, it is still possible to score the plate independently whereupon the file will automatically revert to its original name.

The probe layout should be identical in each plate X and Y for scoring to operate (the second plate will normally be run directly from a previously stored set of parameters, meaning that identical parameters are automatically used).

Match/Mismatch Option

The Probe Selection window allows the user to define the designation of a match or mismatch to a given probe. Thus, where the user is using a probe which will define the polymorphic position to be a "G" (i.e. the probe contains an "A" at this position), clicking on the Match/Mismatch button allows this to be defined. On definition of the match and mismatch, the heterozygote will automatically be entered (e.g. if homozygous match is entered as "A" and heterozygous mismatch is entered as "G", the heterozygote will be entered as "A/G"). This will be automatically entered into the results database screen at the end of the experiment, hence making results easily understandable. Similarly, users wishing to store allele information in the form of number (1, 2 or 1–2) this option is available. Designation of the "Match" homozygote as 1 will automatically designate the other homozygote as 2 and vice-versa. In this embodiment, the heterozygote is always scored as 1_2 when using this option.

Derivative Window Size

In the Probe Selection window, the user is able to set the derivative window size, which defines the number of points from the fluorescence decay curve that will be used to form the negative first derivative curve. This parameter can therefore be set differently for each probe used in an experiment. As the curves produced for a given probe may differ markedly from that produced by another, it is sometimes of benefit to have them smoothed independently. Curve Smoothing is explained below.

Sensitivity Settings

In the Probe Selection window it is possible for the user to define the size of the peak, compared to the size of the highest peak that will be scored by the software with the setting ranging from 1 to 100%.

Curve Smoothing Algorithms

The system is designed to allow maximum flexibility for the user while being simple to use. The fundamental factors affecting scoring are the Match and Mismatch zones as outlined above. While minimal manipulation of the other parameters which affect curve generation is normally required, the system allows the user to dictate the means by which the curves are created (via the input into smoothing parameters etc.) to allow manipulation of scoring as is necessary for a given data-set. Several parameters affect the means by which melting curves are created by the system. The most important of these are smoothing of the raw data curve and smoothing of the negative first derivative curve (via alteration of the smoothing window and derivative window size respectively).

a) Smoothing Window Size

The smoothing window determines how many of the data points from the raw data graph will be used to generate a smoothed version of this curve. A smoothing window size of 1 determines that one point on each side of each of the raw data points is taken to calculate each point of the smoothed curve. This option is found in the Results (Melt Curve) and Probe Selection screens and is applicable to each probe individually.

b) Derivative Window Size

In the Probe Selection screen it is possible to define the number of points from the raw data curve to form the negative first derivative curve from which the melting temperature peaks are scored. A default setting of 2, which equates to 2 points being taken each side of each data point to define the derivative curve, can be altered between values of 1–10. A setting of 1 therefore represents minimal smoothing of the curve, 10 maximum. Experimental results can vary in the degree to which smoothing is required, however it is likely that the optimal settings for scoring of DASH peaks will lie outside the range 1–3.

c) Alternative Smoothing Option

This additional option is available to alter curve generation such that the negative first derivative curve is derived from the smoothed version of the raw data curve (default is preferably generation of the curve from the non-smoothed raw data curve).

Running a DASH Experiment

Figure 10:
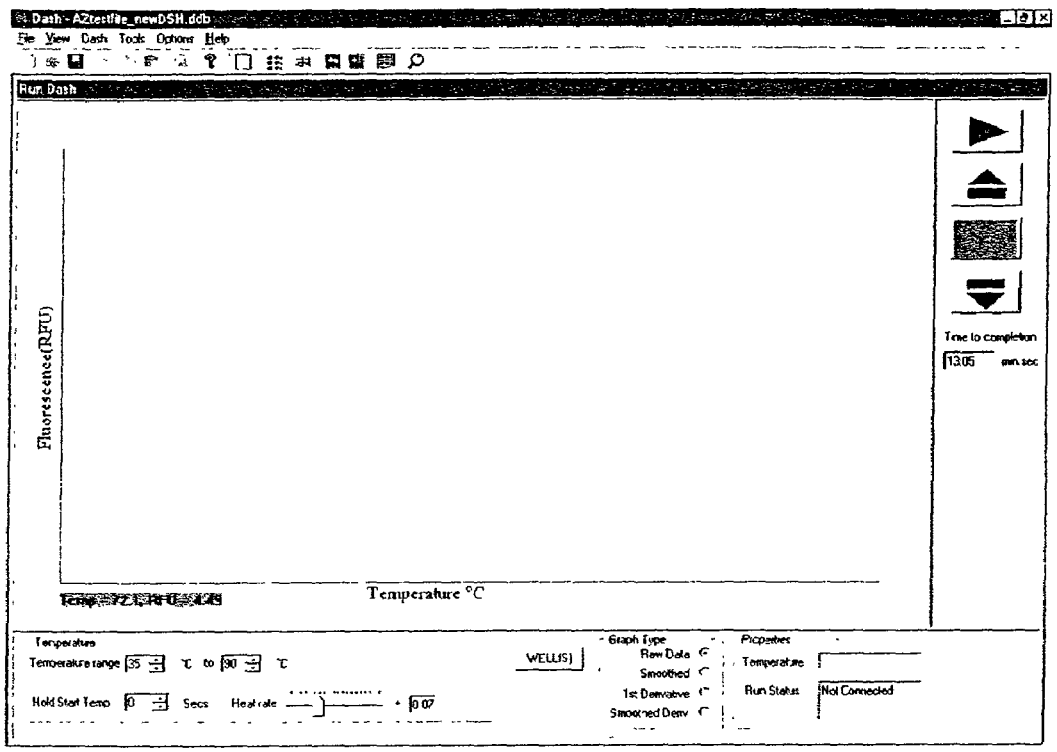
FIG. 10 is a view of an embodiment of experiment display window for setting and controlling experiments.

When it is desired to run an experiment, a "Run" option is selected from an appropriate menu or by an appropriate icon. In the preferred embodiment the screen of FIG. 10 is provided in the first instance.

The screen is used to control the DASH machine, allowing several of the conditions under which the experiment will be run to be varied as desired, prior to initiating the experiment. In particular, the user can control the following conditions:

a) The user may alter the temperatures between which the DASH reaction is run from (in this example) a minimum of between 35–45° C. to a maximum of between 70–90° C. This will be governed by the predicted or experimentally defined melting temperatures of the hybridisation probes. Using this option, the machine will ramp at an optimal speed to the desired temperature before initiation of scanning. Scanning will be performed during heating at a rate defined by the user.

b) The user can choose to alter the heating rate of the experiment between a minimum of 0.01 and a maximum of 0.2° C./s by use of the icon located to the left of the screen below the Graph. Alteration of the ramp rate determines how many readings will be taken through the experiment. The more readings taken, the more data points will be used to form the graphs, hence leading to better-defined curves. A default setting of 0.7° C./second is probably suitable for most experiments. The ramp may be altered by clicking and dragging the pointer using the left mouse button.

c) The user can choose to hold the start temperature for up to 120 seconds in this example. Holding temperature in this way serves to reduce background by allowing secondary structure of the immobilized DNA, and any excess annealed probe, to be denatured prior to running the DASH experiment.

Following adjustment of the run parameters as required, the DASH experiment may be started.

The Run screen (FIG. 10) allows visualization of the fluorescence data from the test in real-time. A choice of graphing types is available, giving the facility to graph raw data, smoothed data, a negative first derivative curve or a smoothed version of the negative first derivative curve. The raw fluorescence data is scaled such that the highest fluorescence is drawn to the top of the graph.

An estimated time to completion of the test is preferably provided, as are the current run properties (current plate temperature and heating/cooling status). A box to the bottom left of the graph gives the temperature and relative fluorescence at the position of the cursor.

Figure 11:
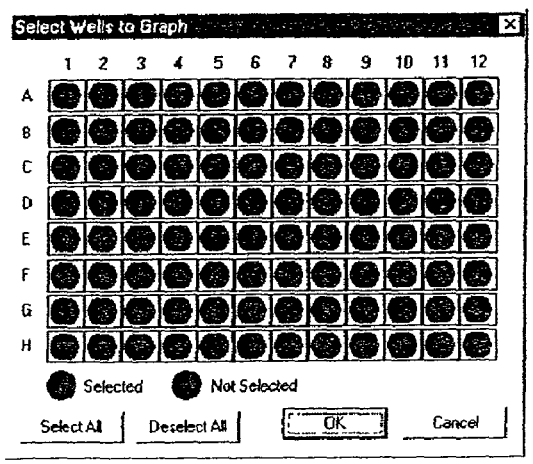
FIG. 11 is a view of a scheme for selecting samples for analysis.

By pressing the WELL(S) icon the samples to be visualized can be selected from a 96 well plates graphic (FIG. 11). By default, all wells are selected.

The up and down arrow keys serve to eject and close the DASH plate respectively. On completion of a DASH experiment, the plate will only eject by default once the temperature has dropped to 80° C. However, the system provides for variation of the temperature at which the plate can be ejected. It also provides for ejection of the plate on completion, thus allowing a higher experimental throughput.

Analyzing the Results from a DASH Experiment

The results are preferably provided in a Results screen accessed by a suitable menu or icon. The preferred screen is shown in FIG. 12.

The Sample Well Layout window shows a color-coded representation of the results. These results are also entered in the Database File. By selecting the appropriate wells on the Sample Layout window, the corresponding entry in the Database will be highlighted and the negative first derivative data is shown as a graph in the Melt Curve window.

Melt Curve Window

By a suitable command (for example a right click of a mouse) the system allows for access to a number of options:

Match Zone, Mismatch Zone and Melt Curve (raw and smoothed) can be switched on and off.

Graph Curves can be shown by their classification (this will highlight the corresponding wells in the Database)

Smoothing and Sensitivity can be optimized. Sensitivity can be set by left clicking on the bar that appears, dragging it to the desired level and left clicking again to drop. For ease of use the ends of the bar are colour coded for the probe being optimized.

Match Zone/Mismatch Zone can be altered/optimized and assigned to a particular probe name.

Quality Scoring

The user can judge the success of the experiment by use of a quality score, displayed on the database screen. This quality score, which is expressed as a percentage, is determined by relation of the size of the peak to other peaks within the experiment derived from the same probe. Thus, the highest peak produced by a given probe and assigned a value of 100 is used to assign percentage values, as a function of peak height, to the other peaks. These values are the same as those used in determining validity of peaks according to the user-assigned sensitivity settings. Whenever the software detects a peak of low quality it will automatically assign a "ck" mark on the appropriate well. This alerts the user to visually check this result as to the reliability of the data.

Graphing Options

Sensitivity settings for peak scoring can be altered by the user.

Should the heterozygote graph data produced resemble inflected curves rather than the more usual double curve these can be scored by switching on a Score Abnormal Heteros option (off by default). Most users will want to generate the negative first derivative from raw data. However, should it be desired to use smoothed data to generate this, then this option is also available.

View Options

At any point in the experiment the system provides for viewing the graph data (raw or $-1^{st}$ derivative).

The scaling of the X-axis can be changed, which will change the view in the Graph/Melt Curve windows. The Y-axis is preferably scaled automatically by the software.

It is also possible to zoom in a particular part of the graph by highlighting the area required on the graph.

Recalculating Results

After an experiment has been carried out the first time for a particular allele and the results automatically generated, it will be necessary to reset peak detection settings, for example if the match and mismatch zones need repositioning.

The system provides this feature by allowing return to the Probe Classification screen and then reposition of the scoring zones to the desired location.

The software will then recalculate the results utilising the new settings. The results can be reviewed. The optimal setting can then be defined and set for use in future experiments performed using the same reagents.

Rerunning DASH Experiments

Within the software there is also the facility to run a DASH experiment with previously used settings.

Saving Data

At any stage the data file can be saved. This is preferably in a format which allows the data to be exported to other software systems, such as database or spreadsheet files.

Oligonucleotide Melting Temperature

The system provides a function for calculating the melting temperatures of PCR primers and the hybridization probe used. This function is very useful during the initial design of oligonucleotide and also for the optimization of run parameters within the DASH system.

Analysis of Results While Running a Separate DASH Experiment

The system also allows the analysis of results of a previous DASH experiment while simultaneously running a new experiment. It also provides for the opening of more than saved file at a time, even while a separate DASH experiment is running in the background.

The analysis system is simple to use and allows the easy selection of probes and the easy reading and interpretation of results. It is also flexible in allowing the reading of many different probes for analysis of a single individual to many different patient samples. Complimentary probing can be incorporated into control to provide absolute confidence in the results obtained.

The system also provides for easy altering of scoring parameters by allowing predicted or experimentally defined probe melting temperatures to be entered either manually or by use of a graphical interface. It also allows for the retrospective alteration of the scoring parameters, as often as the user wishes. This allows precise judgement parameters.

The quality scoring feature draws the attention of the user to samples that should be checked, these being readily accessed, as individual indications of the samples placed.

The system also provides for the reuse of scoring parameters. Experiments can be repeatedly rerun using stored sets of scoring parameters. Parameters from previous tests can be accessed by simply opening the relevant data file and storing the required information. A data experiment can then be run and scored using the formed template with minimal user input.

The invention is not intended to be limited to the methods and materials described above, since these are merely preferred methods and materials rather than mandatory ones. The invention is intended to be limited only by the claims set out below. Thus, the invention encompasses all alternate embodiments that fall literally or equivalently within the scope of these claims.

What is claimed is:

1. A method of detecting DNA variation by monitoring the formation or dissociation of a complex consisting of:
   (a) a single DNA strand of a double stranded DNA of at least 40 base pairs containing the locus of a variation, wherein said single DNA strand is within a monolayer of single DNA strands which are bound to a solid surface,
   (b) an oligonucleotide or DNA analogue probe specific for one allele of the variation and capable of hybridizing to the single strand (a) to form a DNA duplex,
   (c) an intercalating dye specific for the DNA duplex structure of (a) plus (b) which forms a complex with the duplex and reacts uniquely when interacting within the DNA duplex,
which method comprises:
   (1) steadily and progressively adjusting temperature at a rate of between 0.01 to 1° C. per second,
   (2) continually measuring an output signal indicative of interaction of the dye with duplex formed from the strand (a) and probe (b), and
   (3) recording the temperature at which a change in reaction output signal occurs which is attributable to formation or dissociation of the complex and is thereby correlated with the strength with which the probe (b) has hybridized to the single strand (a).

2. A method according to claim 1 including
   (1) forming a series of two or more complexes of the kind defined, each with a probe specific for a different allele of the variation, and
   (2) observing their respective denaturing or annealing conditions (e.g. denaturing or annealing temperatures) so as to distinguish alleles of the variation plus the homozygous or heterozygous state if appropriate.

3. A method according to claim 1, in which the marker is one which fluoresces when intercalated in double stranded DNA.

4. A method according to claim 3, in which the denaturing or annealing point is determined by reference to the first derivative of the fluorescence measurement curve.

5. A method according to claim 3, in which denaturing or annealing point is determined by reference to the second derivative of the fluorescence measurement curve.

6. A method according to claim 1, in which the single strand is bound to the solid surface by a biotin/streptavidin type interaction.

7. A method according to claim 1, in which the complex is formed by adding the probe and marker to the single strand in an appropriate buffer solution.

8. A method according to claim 7, in which the buffer solution is Hepes buffer having a salt concentration less than 200 mM.

9. A method according to claim 1, using a fluorescent intercalating dye, in which the dye is SYBR Green I.

10. A method according to claim 1, in which double stranded DNA is a product of PCR amplification of a target sequence.

11. A method according to claim 10, in which the PCR product is at least 100 base pairs in length.

12. A method according to claim 10, in which the PCR product is from 40 to 100 base pairs in length.

13. A method of detecting DNA variation which comprises
   (1) bringing together:
   (a) a single DNA strand of a double stranded DNA of at least 40 base pairs containing the locus of a variation, wherein said single DNA strand is within a monolayer of single DNA strands which are bound to a solid surface,
   (b) an oligonucleotide or DNA analogue probe specific for one allele of the variation and capable of hybridizing to the single strand (a) to form a DNA duplex,
   (c) an intercalating dye specific for the DNA duplex structure of (a) plus (b) which forms a complex with the said duplex and reacts uniquely when interacting within the duplex,
thereby forming a complex consisting of the components (a), (b) and (c), wherein the components (a), (b), and (c) are brought together under conditions in which either
   (i) the component (a) hybridizes to component (b) and the complex is formed with component (c), or
   (ii) the components (a) and (b) do not hybridize and the complex with component (c) is not formed,
   (2) thereafter steadily and progressively adjusting the temperature at a rate of between 0.01 to 1° C. per second, respectively, either
   (i) to denature the formed DNA duplex and cause dissociation of the complex or
   (ii) to cause formation of the DNA duplex and resulting complex,
   (3) continually measuring an output signal indicative of the extent of hybridization of (a) and (b) and resulting complex formation with (c), and
   (4) recording the temperature at which a change of output signal occurs which is indicative of, respectively,
   (i) dissociation of the complex, or
   (ii) formation of the complex.

14. A method according to claim 13 which comprises
(1) forming a series of two or more complexes of the kind defined, each with a probe specific for a different allele of the variation, and
(2) observing their respective denaturing or annealing conditions (e.g. denaturing or annealing temperatures) so as to distinguish alleles of the variation plus the homozygous or heterozygous state if appropriate.

15. A method according to claim 13, in which the marker is one which fluoresces when intercalated in double stranded DNA.

16. A method according to claim 15, in which the denaturing or annealing point is determined by reference to the first derivative of the fluorescence measurement curve.

17. A method according to claim 15, in which denaturing or annealing point is determined by reference to the second derivative of the fluorescence measurement curve.

18. A method according to claim 13, in which the single strand is bound to the solid surface by a biotin/streptavidin type interaction.

19. A method according to claim 13, in which the complex is formed by adding the probe and marker to the single strand in an appropriate buffer solution.

20. A method according to claim 19, in which the buffer solution is Hepes buffer having a salt concentration less than 200 mM.

21. A method according to claim 13, using a fluorescent intercalating dye, in which the dye is SYBR Green I.

22. A method according to claim 13, in which the double stranded DNA is a product of PCR amplification of a target sequence.

23. A method according to claim 22, in which the PCR product is at least 100 base pairs in length.

24. A method according to claim 22, in which the PCR product is from 40 to 100 base pairs in length.

25. A method of detecting DNA variation which comprises:
(1) forming a complex consisting of:
  (a) a single DNA strand of a double stranded DNA of at least 40 base pairs containing the locus of a variation, wherein said single DNA strand is within a monolayer of single DNA strands which are bound to a solid surface,
  (b) an oligonucleotide or DNA analogue probe specific for one allele of the variation hybridized to the single strand (a) to form a duplex, and
  (c) an intercalating dye specific for the DNA duplex structure of (a) plus (b) and which reacts uniquely when interacting within the DNA duplex, and
(2) continually measuring an output signal of the extent of the resulting reaction of the marker and the duplex while steadily increasing the temperature at a rate of between 0.01 to 1° C. per second,
(3) recording the temperature at which a change in reaction output signal occurs which is attributable to dissociation of the complex and is thereby correlated with the strength with which the probe (b) has hybridized to the single strand (a).

26. A method according to claim 25, which comprises
(1) forming a series of two or more complexes of the kind defined, each with a probe specific for a different allele of the variation, and
(2) observing their respective denaturing or annealing conditions (e.g. denaturing or annealing temperatures) so as to distinguish alleles of the variation plus the homozygous or heterozygous state if appropriate.

27. A method according to claim 25, in which the marker is one which fluoresces when intercalated in double stranded DNA.

28. A method according to claim 27, in which the denaturing or annealing point is determined by reference to the first derivative of the fluorescence measurement curve.

29. A method according to claim 27, in which denaturing or annealing point is determined by reference to the second derivative of the fluorescence measurement curve.

30. A method according to claim 25, in which the single strand is bound to the solid surface by a biotin/streptavidin type interaction.

31. A method according to claim 25, in which the complex is formed by adding the probe and marker to the single strand in an appropriate buffer solution.

32. A method according to claim 31, in which the buffer solution is Hepes buffer having a salt concentration less than 200 mM.

33. A method according to claim 25, using a fluorescent intercalating dye, in which the dye is SYBR Green I.

34. A method according to claim 25, in which the double stranded DNA is a product of PCR amplification of a target sequence.

35. A method according to claim 34, in which the PCR product is at least 100 base pairs in length.

36. A method according to claim 34, in which the PCR product is from 40 to 100 base pairs in length.

37. A method of detecting DNA variation which comprises:
(1) bringing together:
  (a) a single DNA strand of a double stranded DNA of at least 40 base pairs containing the locus of a variation, wherein said single DNA strand is within a monolayer of single DNA strands which are bound to a solid surface,
  (b) an oligonucleotide or DNA analogue probe specific for one allele of the variation and capable of hybridizing to the single strand (a) to form a DNA duplex,
  (c) an intercalating dye specific for the DNA duplex structure of (a) plus (b) and which reacts uniquely when interacting within the duplex,
  the components (a), (b) and (c) being brought together prior to formation of the defined complex and under conditions in which (a) and (b) do not hybridize;
(2) steadily adjusting the temperature at a rate of between 0.01 to 1° C. per second to cause formation of the duplex and resulting complex consisting of components (a), (b), and (c), and
(3) measuring an output signal indicative of the occurrence of hybridization of (a) and (b).

38. A method according to claim 37, which comprises
(1) forming a series of two or more complexes of the kind defined, each with a probe specific for a different allele of the variation, and
(2) observing their respective denaturing or annealing conditions (e.g. denaturing or annealing temperatures) so as to distinguish alleles of the variation plus the homozygous or heterozygous state if appropriate.

39. A method according to claim 37, in which the marker is one which fluoresces when intercalated in double stranded DNA.

40. A method according to claim 39, in which the denaturing or annealing point is determined by reference to the first derivative of the fluorescence measurement curve.

41. A method according to claim 39, in which denaturing or annealing point is determined by reference to the second derivative of the fluorescence measurement curve.

42. A method according to claim 37, in which the single strand is bound to the solid surface by a biotin/streptavidin type interaction.

43. A method according to claim 37, in which the complex is formed by adding the probe and marker to the single strand in an appropriate buffer solution.

44. A method according to claim 43, in which the buffer solution is Hepes buffer having a salt concentration less than 200 mM.

45. A method according to claim 37, using a fluorescent intercalating dye, in which the dye is SYBR Green I.

46. A method according to claim 37, in which the double stranded DNA is a product of PCR amplification of a target sequence.

47. A method according to claim 46, in which the PCR product is at least 100 base pairs in length.

48. A method according to claim 46, in which the PCR product is from 40 to 100 base pairs in length.

49. A method according to claim 4 comprising determining the presence, in the negative of said derivative of the fluorescent measurement curve, one or both of: a first peak associated with the denaturing of a match probe target duplex and a second peak associated with the presence of a mis-match probe target duplex.

50. A method according to claim 16 comprising determining the presence, in the negative of said derivative of the fluorescent measurement curve, one or both of: a first peak associated with the denaturing of a match probe target duplex and a second peak associated with the presence of a mis-match probe target duplex.

51. A method according to claim 28 comprising determining the presence, in the negative of said derivative of the fluorescent measurement curve, one or both of: a first peak associated with the denaturing of a match probe target duplex and a second peak associated with the presence of a mis-match probe target duplex.

52. A method according to claim 40 comprising determining the presence, in the negative of said derivative of the fluorescent measurement curve, one or both of: a first peak associated with the denaturing of a match probe target duplex and a second peak associated with the presence of a mis-match probe target duplex.

53. A method of detecting DNA variation by monitoring the formation or dissociation of a complex consisting of:
(a) a single DNA strand of a double stranded DNA of at least 40 base pairs containing the locus of a variation, bound within a two dimensional monolayer on the surface of a solid support,
(b) an oligonucleotide or DNA analogue probe specific for one allele of the variation and capable of hybridizing to the single strand (a) to form a DNA duplex, and;
(c) an intercalating dye specific for the DNA duplex structure of (a) plus (b) which forms a complex with the said duplex and reacts uniquely when interacting within the DNA duplex, which method comprises:
(i) steadily and progressively adjusting the temperature at a rate of between 0.01 to 1° C. per second,
(ii) continually measuring an output signal indicative of interaction of the dye with duplex formed from the strand (a) and probe (b), and
(iii) recording the temperature at which a change in reaction output signal occurs which is attributable to formation or dissociation of the complex and is thereby correlated with the strength with which the probe (b) has hybridized to the single strand (a).

54. The method of claim 53 wherein the single DNA strand is bound to the surface of the support by a biotin/streptavidin type interaction.

55. The method of claim 53 wherein the complex is formed by adding the probe and the marker to the single strand in a buffer having a salt concentration less than 200 mM.

56. A method of detecting DNA variation by monitoring the formation or dissociation of a plurality of complexes, each said complex consisting of:
(a) a single DNA strand of a double stranded DNA of at least 40 base pairs containing the locus of a variation,
(b) an oligonucleotide or DNA analogue probe specific for one allele of the variation and capable of hybridizing to the single strand (a) to form a DNA duplex, and;
(c) an intercalating dye specific for the DNA duplex structure of (a) plus (b) which forms a complex with the said duplex and reacts uniquely when interacting within the DNA duplex, wherein each said complex is bound to a surface of a solid support and said plurality of complexes form a monolayer on said surface, which method comprises:
(i) steadily and progressively adjusting the temperature at a rate of between 0.01 to 1° C. per second,
(ii) continually measuring an output signal indicative of interaction of the dye with duplex formed from the strand (a) and probe (b), and
(iii) recording the temperature at which a change in reaction output signal occurs which is attributable to formation or dissociation of the complex and is thereby correlated with the strength with which the probe (b) has hybridized to the single strand (a).

57. The method of claim 56 wherein the single DNA strand is bound to the surface of the support by a biotin/streptavidin type interaction.

58. The method of claim 56 wherein the complex is formed by adding the probe and the marker to the single strand in a buffer having a salt concentration less than 200 mM.

* * * * *